United States Patent
Hayashi

Patent Number: 5,944,664
Date of Patent: Aug. 31, 1999

[54] METHOD OF MEASURING THE AMOUNT OF DISLOCATION OF CERVICAL VERTEBRAE

[75] Inventor: Masayuki Hayashi, Nagoya, Japan

[73] Assignee: Kazuyuki Hayashi, Nagoya, Japan; a part interest

[21] Appl. No.: 09/001,034

[22] Filed: Dec. 30, 1997

[30] Foreign Application Priority Data

May 22, 1997 [JP] Japan ................................. 9-150190

[51] Int. Cl.⁶ .................................................. A61B 6/00
[52] U.S. Cl. ........................... 600/425; 382/132; 382/128
[58] Field of Search ................................. 600/425, 407; 382/132, 128; 378/53, 54, 4

[56] References Cited

U.S. PATENT DOCUMENTS

| | | | |
|---|---|---|---|
| 4,899,761 | 2/1990 | Brown et al. | 128/781 |
| 5,582,186 | 12/1996 | Wiegard | 128/782 |
| 5,602,935 | 2/1997 | Yoshida et al. | 382/132 |

*Primary Examiner*—Marvin M. Lateef
*Assistant Examiner*—Eleni Mantis Mercader
*Attorney, Agent, or Firm*—Kubovcik & Kubovcik

[57] ABSTRACT

A method of measuring the amount of dislocation of the cervical vertebrae of the patient includes a step of defining, on the base posterior view, an end point on a line connecting a point representing the front end of the nasal septum and a point being equidistant from a pair of ocular orbits; a step of determining, on each side of the base posterior view, a point of intersection (or contact) of the "profile of a foramen magnum of a skull" and the region where a condyle of the skull is joined to, or in close proximity to, a superior articular pit of atlas; and a step of defining, on the base posterior view, a bisector of the angle which a line connecting the front end point to one of the points of origin forms with respect to another line connecting the front end point to the other of the points of origin. The amount of dislocation of the cervical vertebrae is determined by means of the bisector. In the case of the atlas, points of foramen transversariums representing points of the substantial center of the foramen transversariums of the atlas are defined on the image of the base posterior view. The amount of dislocation of the atlas is calculated by measuring the distance between one point of foramen transversarium and the bisector and the distance between the other point of foramen transversarium and the same.

30 Claims, 24 Drawing Sheets

From step S16 shown in Fig.1 and Fig.2

To step S17 shown in Fig.1 and Fig.2

METHOD OF MEASURING THE AMOUNT OF DISLOCATION OF CERVICAL VERTEBRAE

BACKGROUND OF THE INVENTION

1. Field of the Invention

The present invention relates to a method of measuring the amount of dislocation of cervical vertebrae of the human body.

2. Description of the Related Art

It is already known that the dislocation of the vertebrae (the atlas, the axis etc) from their original positions results in various diseases or in the body being brought into bad physical condition. To prevent such a problem, it is commonly practiced, particularly in the field of chiropractic, to correct the cervical vertebrae.

Lateral dislocation and rotational dislocation are critical in correcting the dislocation of the vertebrae. A so-called Duff method by which the chiropractor examines the dislocation of the vertebrae by touch is known as an existing method of determining the dislocation of the vertebrae. More specifically, the Duff method is a method of detecting the center of the foramen magnum through use of the point of origin of a V-shaped area defined between the profile of the fundus of an occipital bone and the profile of an occipital condyle.

However, it is impossible to numerically express the correct amount of dislocation by the existing method of measuring the amount of dislocation or by the existing method in which the dislocation is examined by touch. Further, the amount of dislocation cannot be measured by the Duff method unless the V-shaped area is clearly seen in an X-ray film.

SUMMARY OF THE INVENTION

Accordingly, it is a primary object of the present invention to provide a method which enables accurate measurement of the amount of dislocation of the cervical vertebrae.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing object, in accordance with a first aspect of the present invention, there is provided a method of measuring the amount of dislocation of the cervical vertebrae of a person, the method including:

an end point determination step of determining, on the base posterior view, an end point on a line which connects a point representing the front end of the nasal septum to a point being equidistant from a pair of ocular orbits;

a point-of-origin-determination step of determining, on each side of the base posterior view, a point of intersection (or contact) of the "profile of a foramen magnum of a skull" and the region where a condyle of the skull is joined to, or in close proximity to, a superior articular pit of the atlas (the first cervical vertebra); and a bisector determination step of defining, on the base posterior view, a bisector of the angle which a line connecting the front end point to one of the points of origin forms with respect to another line connecting the front end point to the other one of the points of origin.

According to the method of measuring the amount of dislocation of the cervical vertebrae, in the front end point determination step, there is determined, on the base posterior view, an end point on a line which connects a point representing the front end of the nasal septum to a point being equidistant from a pair of ocular orbits. In the point-of-origin determination step, there is determined, on each side of the base posterior view, a point of intersection (or contact) of the "profile of a foramen magnum of a skull" and the region where a condyle of the skull is joined to, or in close proximity to, a superior articular pit of the atlas. In the bisector determination step, there is determined, on the base posterior view, a bisector of the angle which a line connecting the front end point and one of the points of origin forms with respect to another line connecting the front end point to the other one of the points of origin.

As previously mentioned, the center line used for measuring dislocation of the cervical vertebrae, more particularly the center line of the cervical vertebrae of the foramen magnum, is obtained by determination of the bisector, and hence the dislocation of the cervical vertebrae can be measured by utilization of the thus obtained center line.

Further, the present invention provides a method of measuring the amount of dislocation of the cervical vertebrae of a person, the method including:

an end point determination step of determining, on the base posterior view, an end point on a line which connects a point representing the front end of the nasal septum to a point being equidistant from a pair of ocular orbits;

a point-of-origin-determination step of determining, on each side of the base posterior view, a point of intersection (or contact) of the profile of an inferior articular surface of the atlas and the profile of a front portion of the superior articular surface and a dens of the axis; and a bisector determination step of defining, on the base posterior view, a bisector of the angle which a line connecting the front end point to one of the points of origin forms with respect to another line connecting the front end point to the other one of points of origin.

According to the method of measuring the amount of dislocation of the cervical vertebrae, in the front end point determination step, there is determined, on the base posterior view, an end point on a line which connects a point representing the front end of the nasal septum to a point being equidistant from a pair of ocular orbits. In the point-of-origin determination step, there is determined, on each side of the base posterior view, a point of intersection (or contact) of "the profile of an inferior articular surface of the atlas" and "the profile of a front portion of the superior articular surface and a dens of the axis." In the bisector determination step, there is determined, on the base posterior view, a bisector of the angle which a line connecting the front end point and one of the points of origin forms with respect to another line connecting the front end point to the other one of the points of origin.

As previously mentioned, the center line used for measuring dislocation of the cervical vertebrae is obtained by determination of the bisector, and hence the dislocation of the cervical vertebrae can be measured by utilization of the thus-obtained center line.

Preferably, the method further includes an inter-foramen-transversarium line determination step of defining, on the image of the base posterior view, points of foramen transversariums which represent points of the substantial center of the foramen transversariums of the atlas, and of drawing a line connecting together these points (simply referred to as an inter-foramen-transversarium line throughout the specification). The amount of dislocation of the atlas can be calculated from the inter-foramen-transversarium line.

Preferably, the method further includes a point-of-origin connection line step of drawing a line connecting a pair of points of origin which represent the base ends of the profile of the dens of the axis (the second cervical vertebra) [the line being simply referred to as a point-of-origin connection line throughout the specification]. As a result, the amount of dislocation of the axis can be determined from the point-of-origin connection line.

Preferably, the image of the base posterior view is displayed on an X-ray film, and the foregoing points and lines are written on the X-ray film. As a result, the amount of dislocation of the cervical vertebrae can be determined through use of the X-ray film on which the base posterior view is displayed.

Preferably, the method further includes a step of calculating the lateral dislocation of the atlas. In this step, the amount of lateral dislocation of the atlas is calculated by measurement of a distance between one point of foramen transversarium and the point of intersection of the inter-transversarium line and the bisector and of a distance between the other point of foramen transversarium and the point of the intersection.

Preferably, the method further includes a step of calculating the rotational dislocation of the atlas. In this step, the amount of rotational dislocation of the atlas can be measured by measuring an angle which the inter-foramen-transversarium line forms with respect to the line connecting the point of intersection to one point of foramen transversarium and another angle which the inter-foramen-transversarium line forms with respect to the line connecting the point of intersection to the other point of foramen transversarium.

Preferably, the method further includes a point-of-origin connection line step of drawing a line connecting together a pair of points of origin which represent the base ends of the profile of the dens of the axis. The amount of the dislocation of the axis can be calculated by the point-of-origin connection line.

Preferably, the method further includes a step of calculating the lateral dislocation of the axis. In this step, the amount of lateral dislocation of the axis is calculated by measurement of a distance from one of the points of origin to the point of intersection of the bisector and the point-of-origin connection line, as well as of a distance from the other one of the points of origin to the point of intersection of the bisector and the point-of-origin connection line.

Preferably, the method further includes a step of calculating the rotational dislocation of the axis. In this step, the amount of rotational dislocation of the axis is calculated by measuring the angle which the bisector forms with respect to the point-of-origin connection line.

Still other objects of the present invention will become readily apparent to those skilled in the art from the following description wherein there is shown and described a preferred embodiment of this invention, simply by way of illustration of one of the mode best suited to carry out the invention. As it will be realized, the invention is capable of other different embodiments, and its several details are capable of modifications in various, obvious aspects all without departing from the invention. Accordingly, the drawing and descriptions will be regarded as illustrative in nature and not as restrictive.

BRIEF DESCRIPTION OF THE DRAWINGS

The accompanying drawings incorporated herein and forming a part of the specification, illustrate several aspects of the present invention, and together with the description serve to explain the principles of the invention. In the drawings.

Reference will now be made in detail to the present preferred embodiment of the invention, an example of which is illustrated in the accompanying drawings.

DESCRIPTION OF THE PREFERRED EMBODIMENT

By reference to the accompanying drawings, a preferred embodiment of the present invention will be described in detail hereinbelow.

Figure 1:
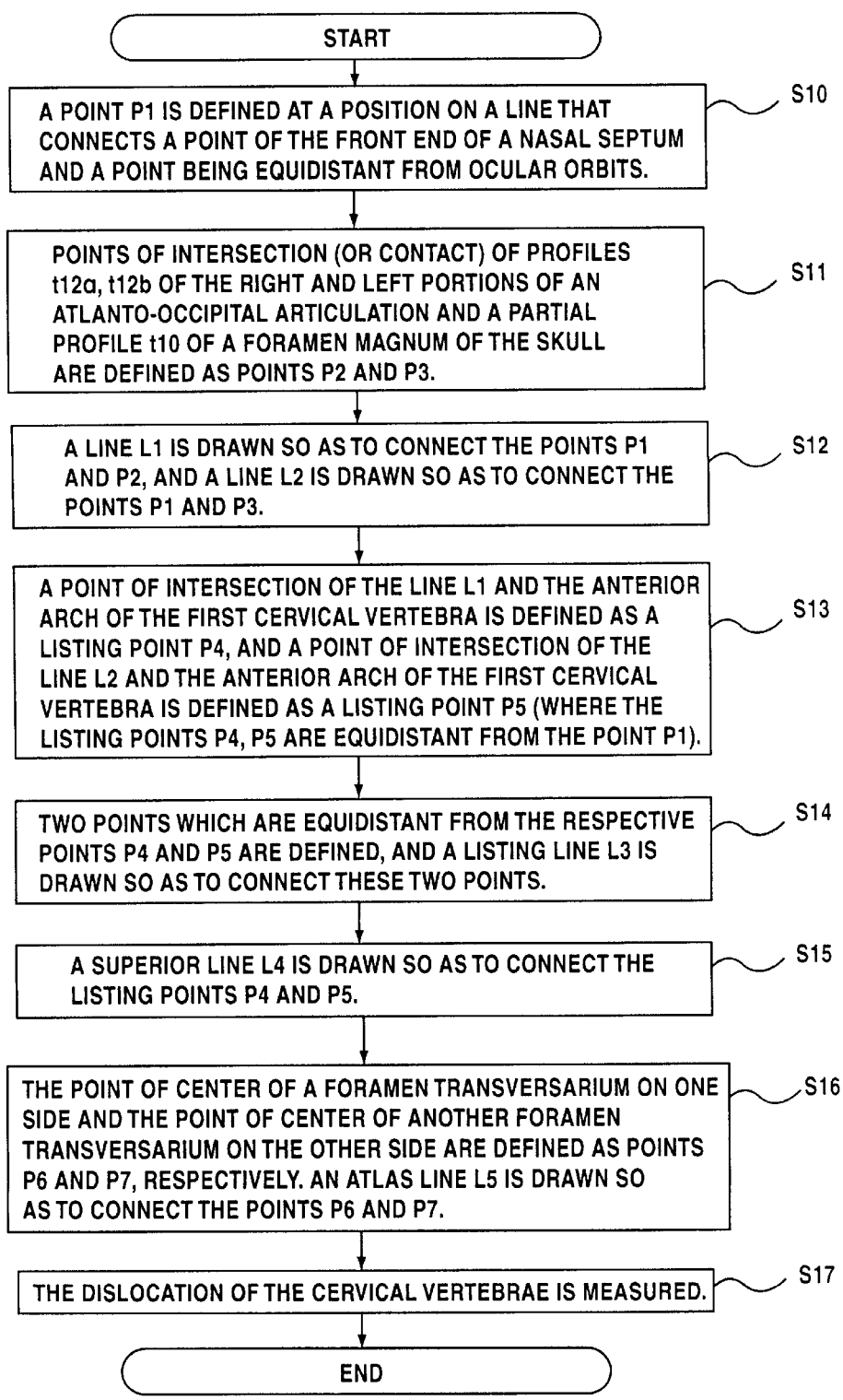
FIG. 1 is a flowchart illustrating a method of measuring the amount of dislocation of cervical vertebrae in accordance with one embodiment of the present invention.
Figure 8:
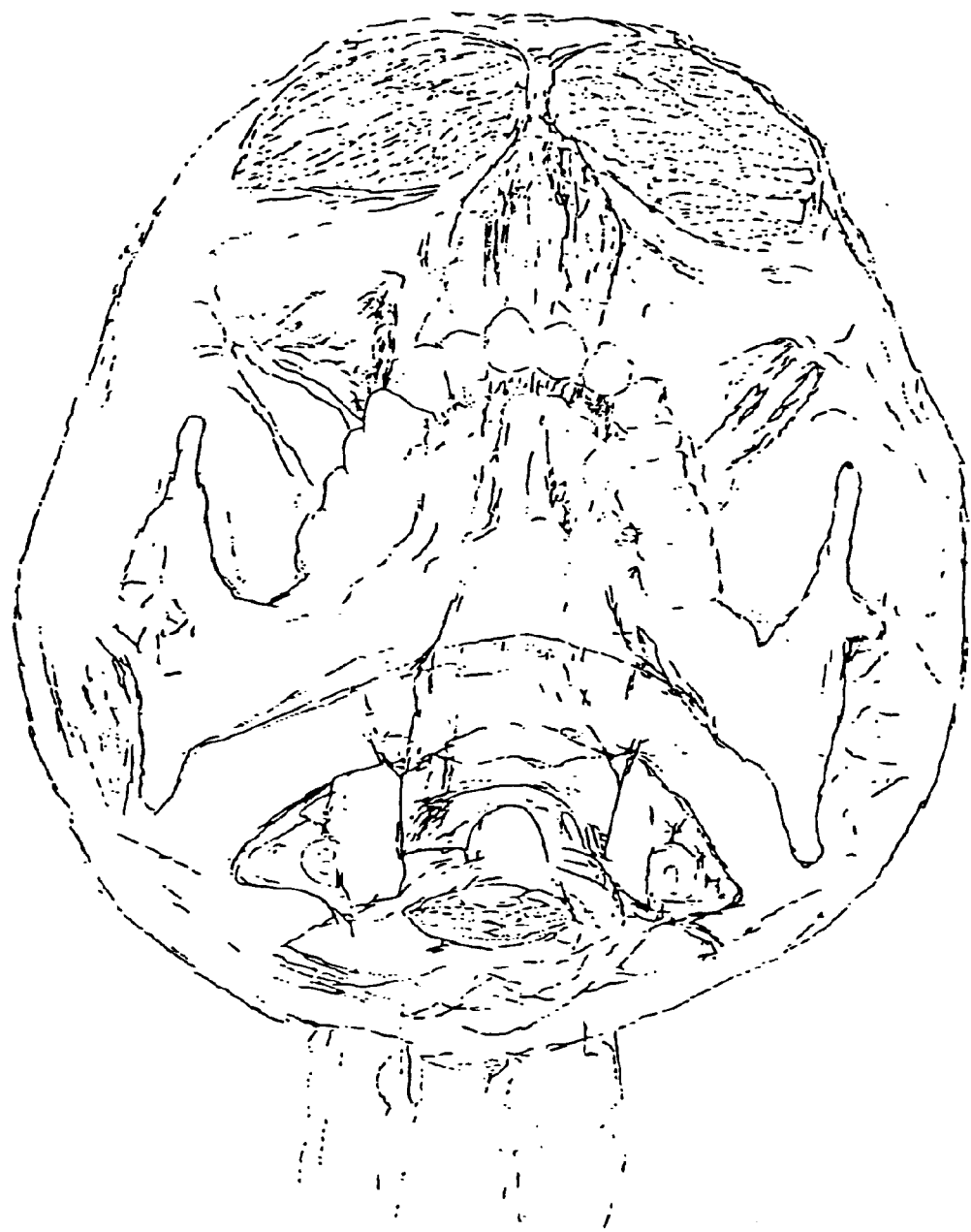
FIG. 8 is a schematic representation illustrating one example of the base posterior view.

A method of measuring the amount of dislocation of the cervical vertebrae in accordance with the present invention is performed in the order of steps shown in FIG. 1. The method of measuring the amount of dislocation of the cervical vertebrae is carried out in accordance with an X-ray film shown in FIG. 8. This X-ray film shown in FIG. 8 is called a base posterior view.

First, an explanation will be given of the base posterior view. This base posterior view is also referred to as an axial view or a vertex view; namely, a view of the human head when it is photographed from the front at an elevated angle from a lower position.

By reference to FIG. 7, the base posterior view will be described in more detail. X-rays enter the head from the side of the mandible to the rear portion of the head after having passed through the antilobium (i.e., the external auditory meatus). The center of the X-rays passes through the external acoustic meatus by way of an intermediate point between the end of the mandible and the angle of the mandible and is arranged so as to fall on the position 1 cm below the center of an X-ray film F. The center of the X-rays falls on the X-ray film F at right angles. Further, the focal length of the X-ray photography is set to 36 inches (about 91 cm). Further, a Pottery-Bucky grid is positioned at an angle of 90° with reference to the axis (the second cervical vertebra) of the center of the X-rays and is usually set to an angle ranging from about 35° to 45° with reference to the floor. The head is fixed at the temples during photography. In short, the head is photographed at such an angle as shown in FIG. 7.

Figure 7:
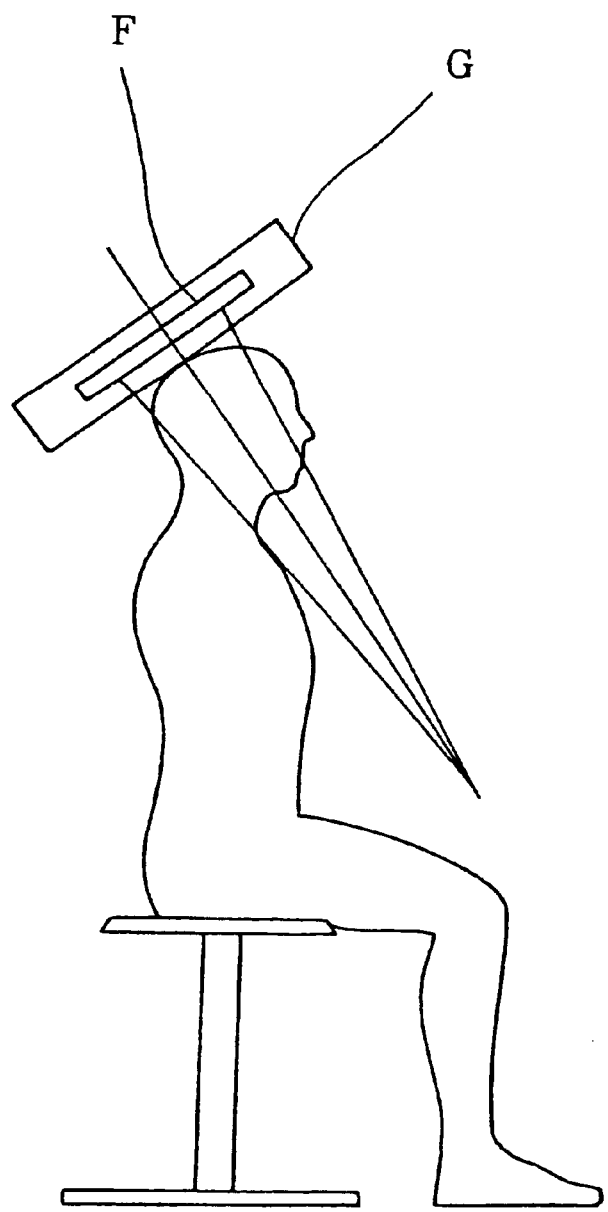
FIG. 7 is a descriptive illustration of a base posterior view.

An actually-used X-ray film is a reversal of the film photographed in the manner as shown in FIG. 7. More specifically, the right-hand side portion of the developed X-ray film shows the actual right-hand side of the patient, whereas the left-hand side portion of the film shows the actual left-hand side of the patent. If a certain portion of the bone of the patient is dislocated to the right in the X-ray film, the corresponding portion of the actual bone is dislocated to the right.

Next, the method of measuring the dislocation of cervical vertebrae will be described specifically. Measurement information to be described later will be written on the X-ray film at the time of measurement of dislocation of the cervical vertebrae. In the following descriptions, the X-ray film which shows the base posterior view corresponds to the image of the base posterior view.

Figure 9:
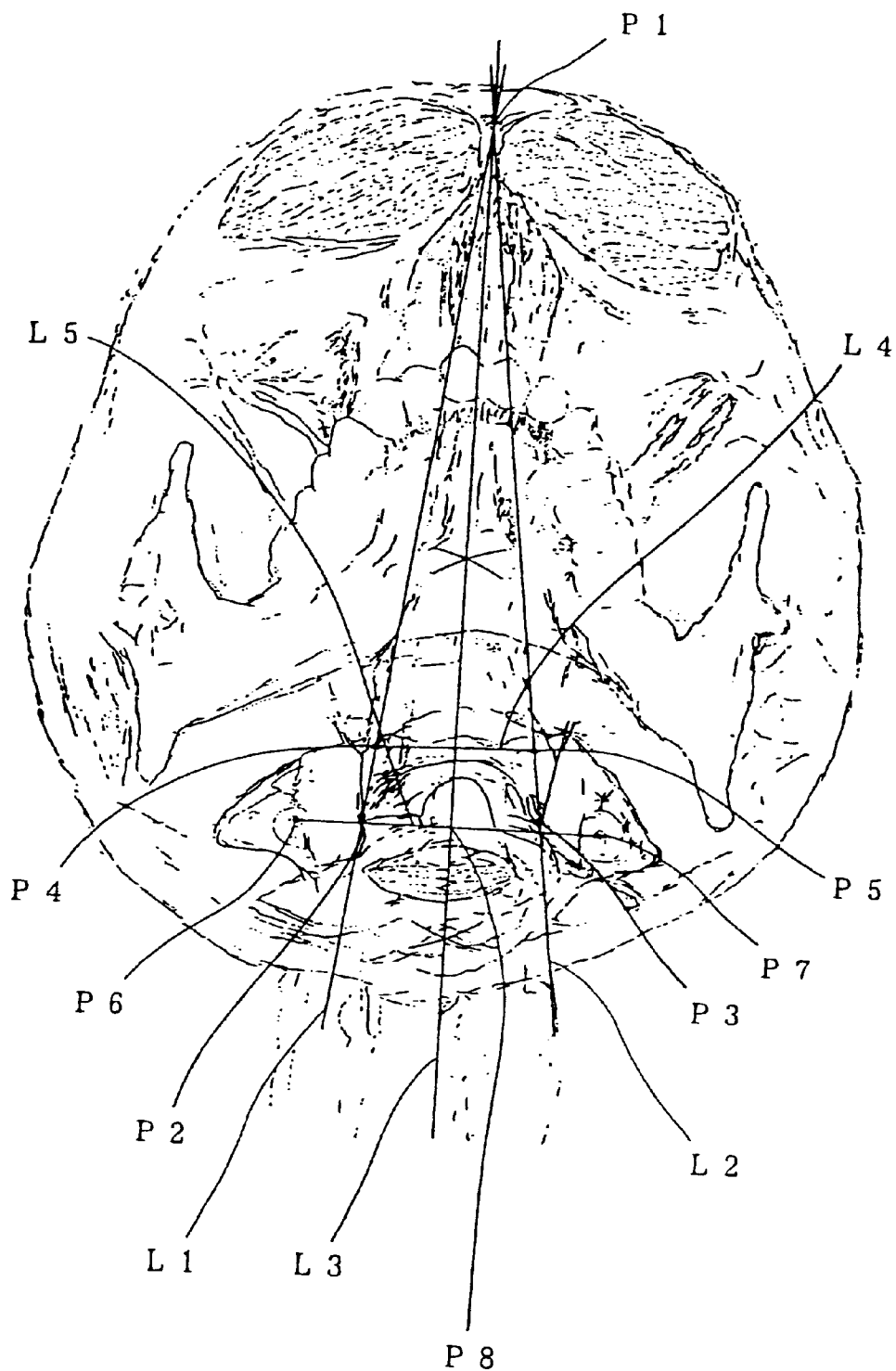
FIG. 9 is a schematic representation illustrating the base posterior view having measurement information entered therein.
Figure 10:
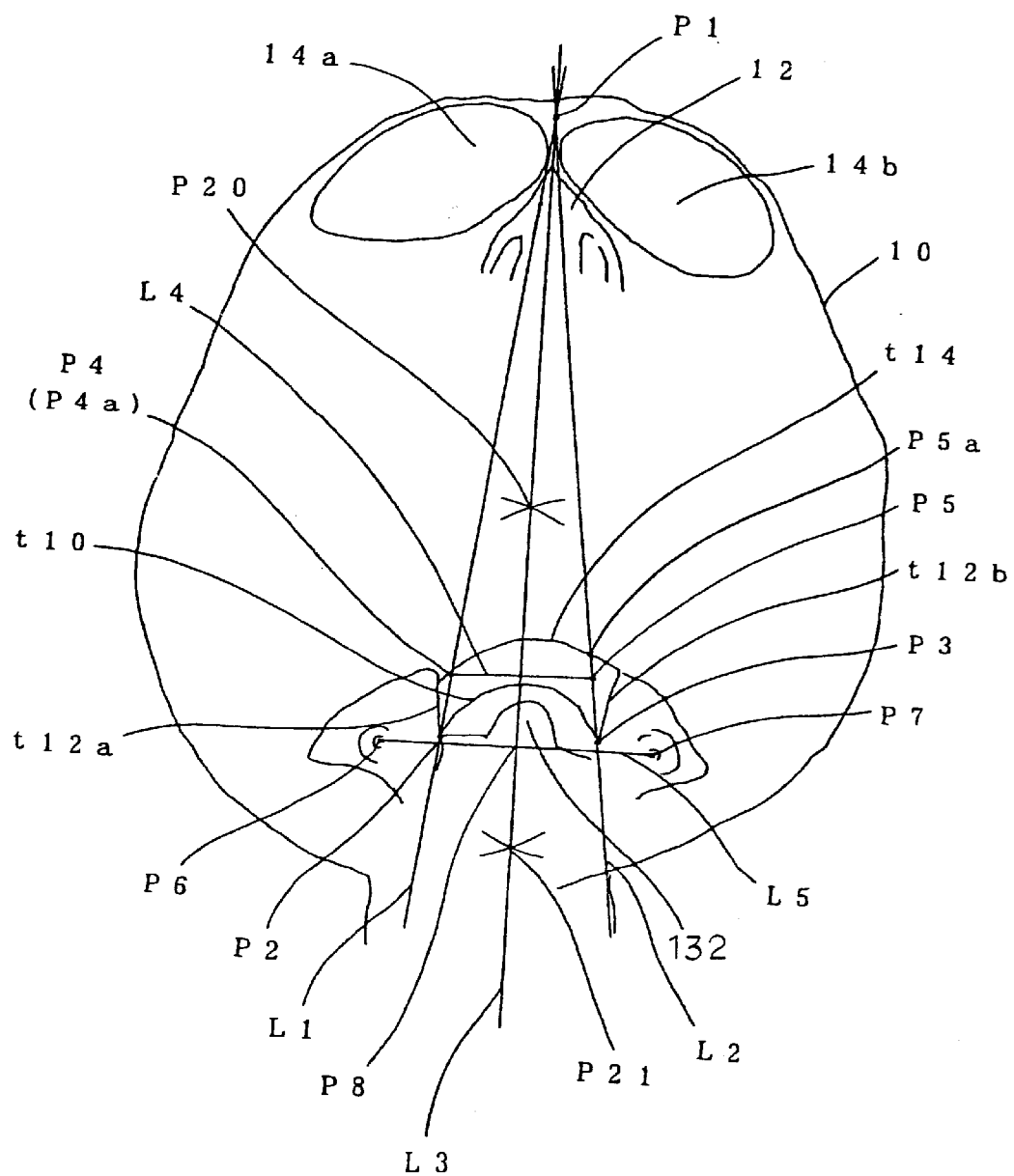
FIG. 10 is a diagrammatic representation for explaining the method of measuring the amount of dislocation of the cervical vertebrae.
Figure 11:
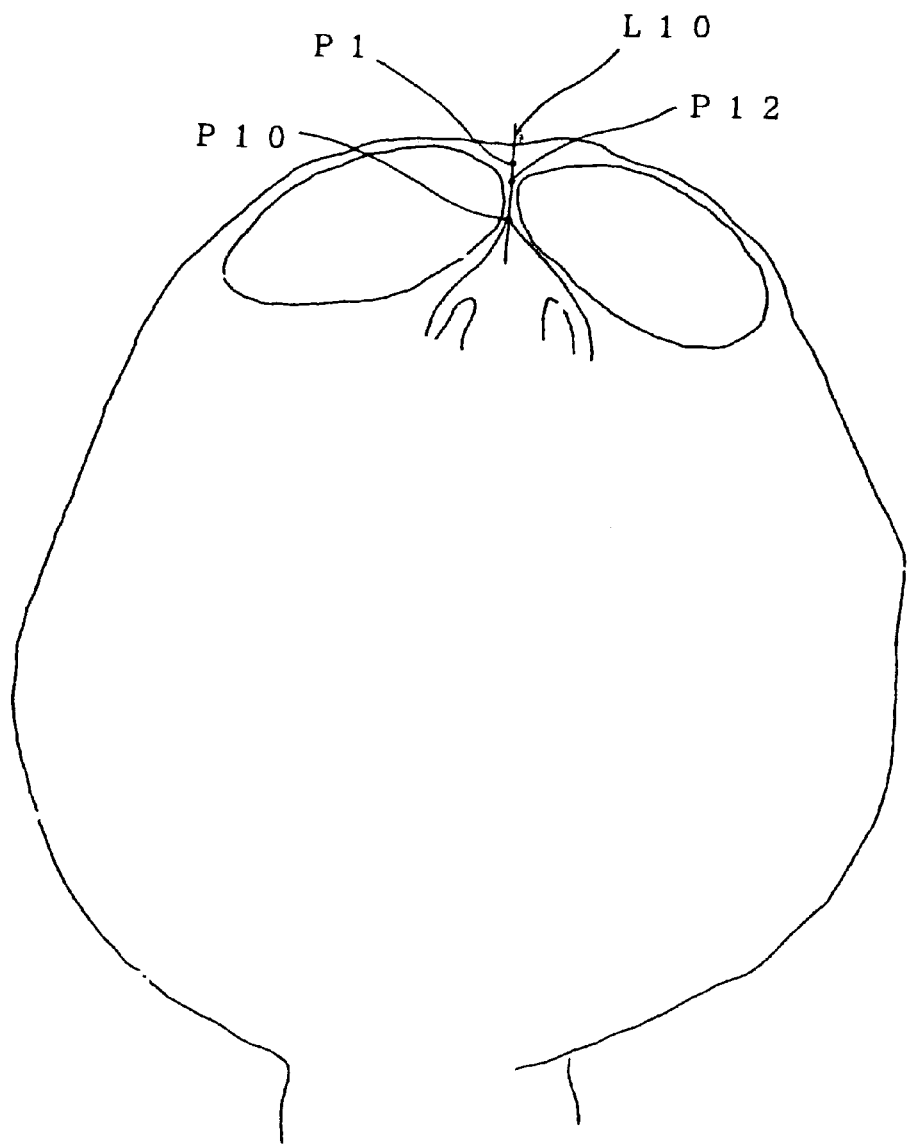
FIG. 11 is a view similar to FIG. 10.

As shown in FIGS. 8 through 11, a point P1 is defined at a certain position on a line L10 (serving as a median line) that connects a point P10 (representing the front end of a nasal septum 12) to a point P12 being equidistant from a pair of ocular orbits 14a, 14b (S10 in FIG. 1). More specifically, the point P12 is equidistant from the points which are in closest proximity to each other on the outer peripheries of the ocular orbits 14a, 14b. As shown in FIG. 11, the thus-determined point P1 is written on the X-ray film of the base posterior view and corresponds to the point of the front end. This step S10 corresponds to an end point determination step.

Next, an intersection of a profile t12a of the left portion of an occipital atlanto articulation and a partial profile t10 of the foramen magnum of a skull 100 (or a point of contact between the profile t12a and the partial profile t10) is defined as a point P2 (S11 in FIG. 1, and see FIGS. 9 and 10). Similarly, an intersection of a profile t12b of the right portion of the occipital atlanto articulation and the partial profile t10 (or a point of contact between the profiles t12b and the partial profile t10) is defined as a point P3. The thus-defined points P2 and P3 are taken as the points of origin on both sides.

Figure 17:
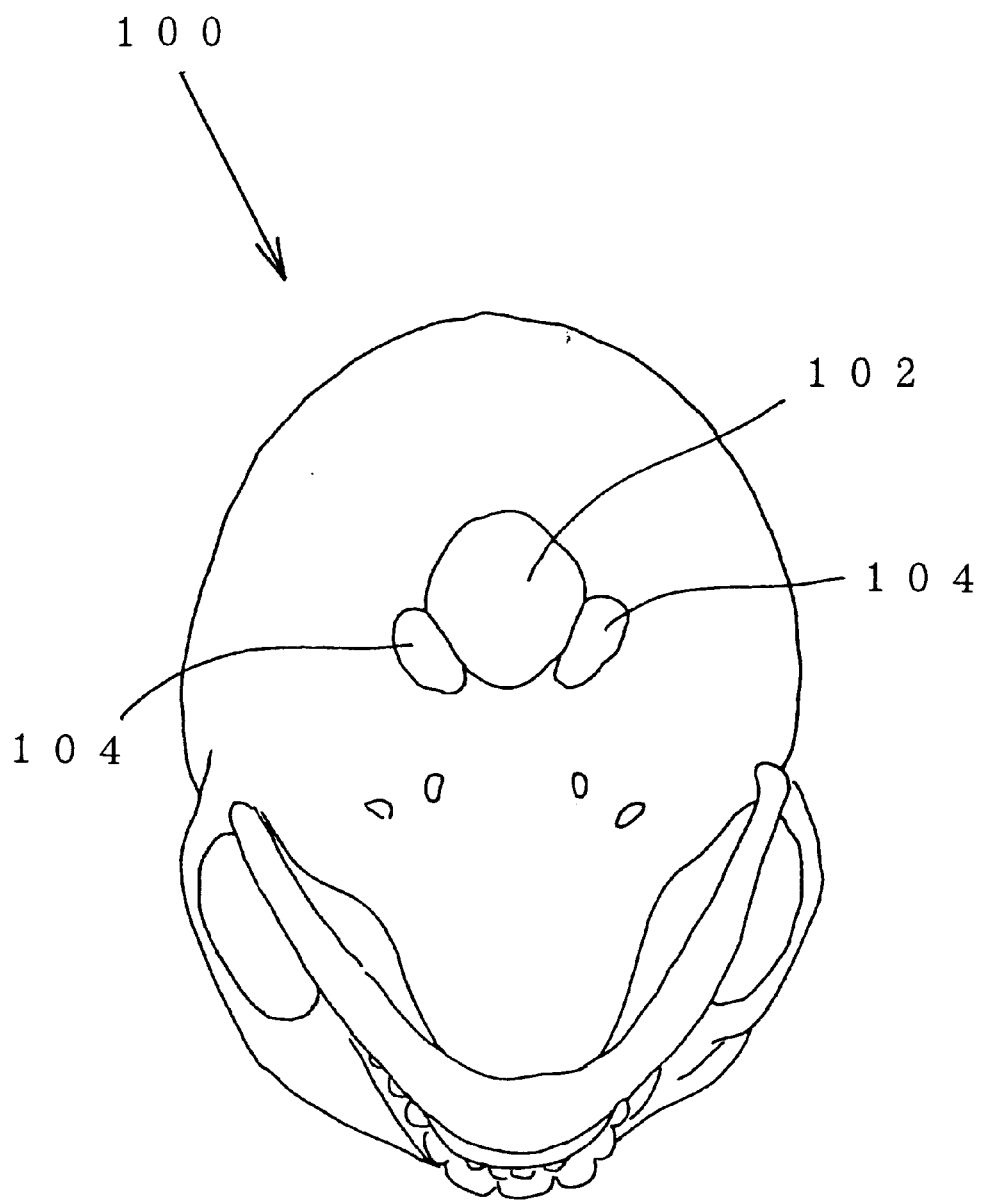
FIG. 17 is a bottom view showing the skull.
Figure 18:
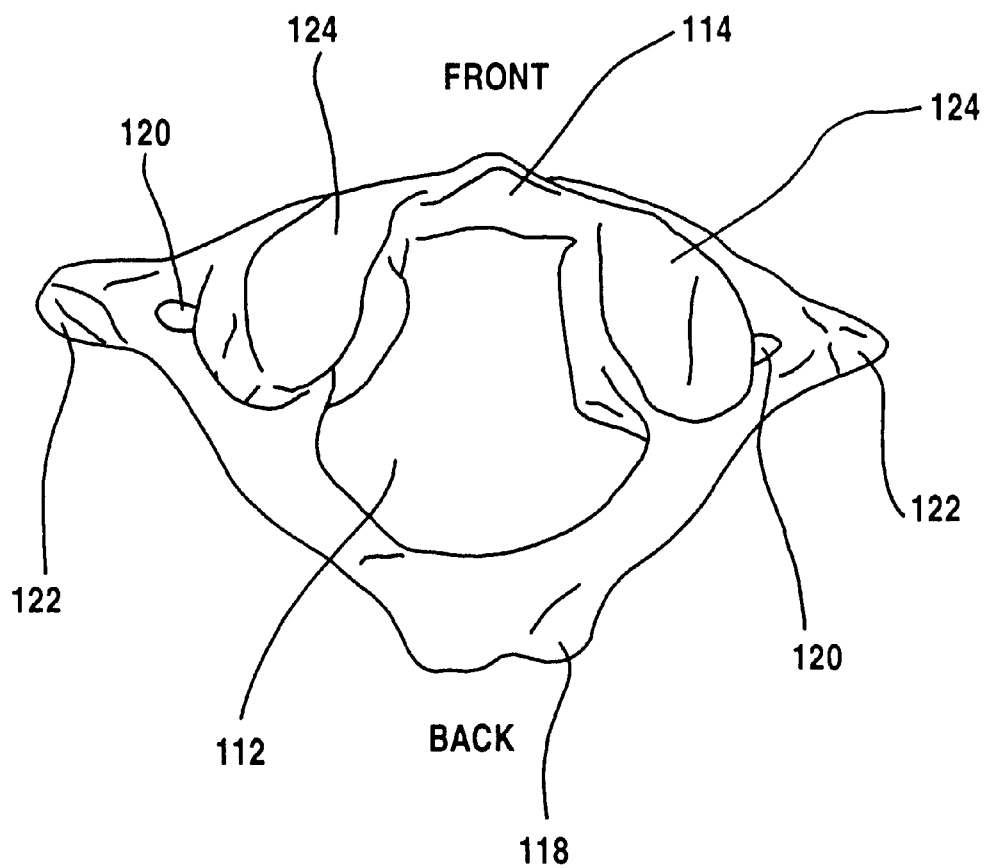
FIG. 18 is a plan view showing the atlas.

The term "occipital atlanto articulation" used herein represents the junction here condyles 104 of the skull 100 (see FIGS. 15 and 17) are joined to superior rticular pits 124 of the atlas (the first cervical vertebra)(see FIG. 18). The profiles 12a, t12b shown in FIG. 10 represent a part of the profile of this junction.

Figure 20:
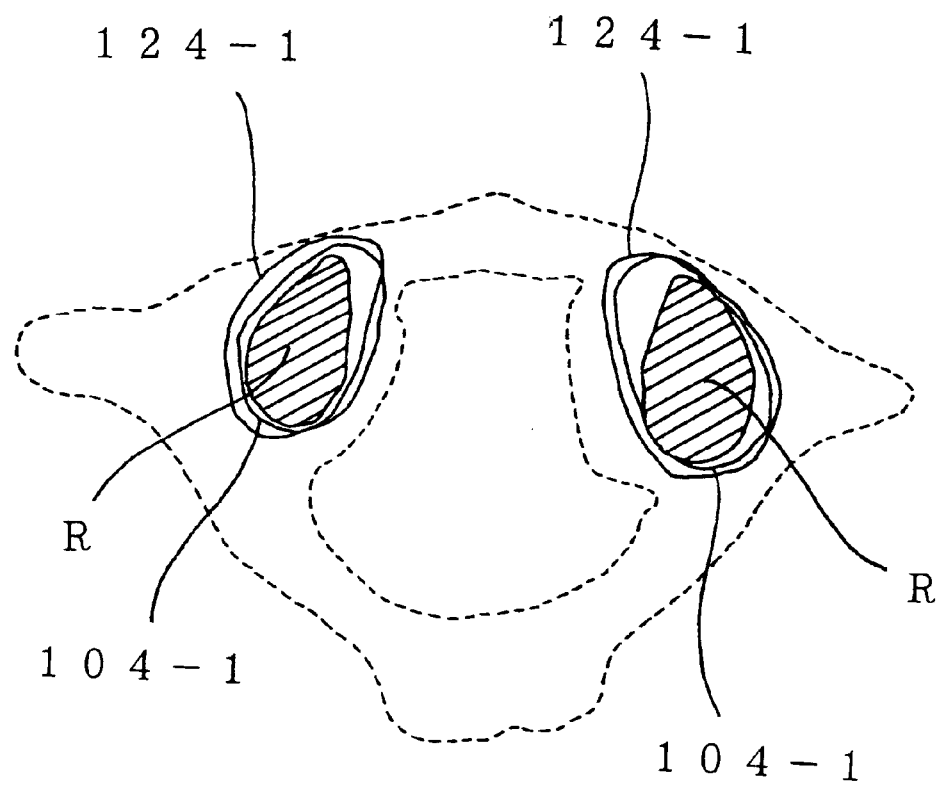
FIG. 20 is a schematic representation showing a junction between a condyle of the skull and a superior articular pit of the atlas.
Figure 21:
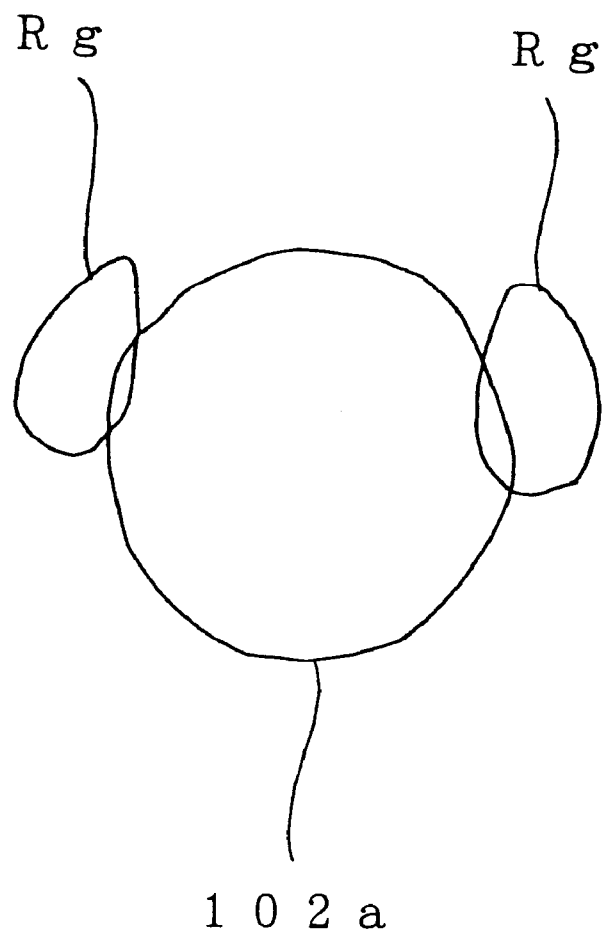
FIG. 21 is a diagrammatic representation showing points of origin.

More specifically, the condyles 104 protrude from both ends of the foramen magnum of the skull 100 and have a smooth curved surface. The superior articular pits 124 are formed into smooth recesses so as to supportingly receive the condyles 104. FIG. 20 shows a profile 124-1 of the superior articular pit 124 of the atlas 110 and a profile 104-1 of the condyle 104 while the condyle 104 is joined to the superior articular pit 124. The junction between the condyle 104 and the superior articular pit 124 is represented by a hatched area R (hereinafter referred to as a junction area R). The profiles t12a, t12b designate a part of the outer periphery Rg of this junction area R. As shown in FIG. 21, with regard to the junction area R on each side, there are two points of the intersection of the outer periphery Rg and a profile 102a of the foramen magnum (a part of which is represented as the partial profile t10). For example, one of the two points on one side is defined as the point P2, and one of the two points on the other side is defined as the point P3. As shown in FIG. 21, although there are two points of intersection of the outer periphery Rg and the profile 102a on each side, there may be a case where merely one point of contact is formed on each side as a result of the outer periphery Rg coming into contact with the profile 102a.

On an actual X-ray film, the junction areas R are indicated in the form of slightly-intense white areas at substantially-symmetrical positions about a dens 132 of the axis 130. Further, there may be a case where the points P2, P3 are indicated as noticeably-white points on the outer periphery Rg of the junction area R. Although the occipital atlanto articulation has been described as the junction where the condyle 104 of the skull 100 is joined to the superior articular pit 124 of the atlas 110, the occipital atlanto articulation actually includes the region where the plane of the condyle 104 is in proximity to the plane of the superior articulation pit 124. In short, the points P2, P3 represent the points of intersection (or contact) of the "profile of the region where the condyle 104 of the skull 100 are joined to, or in close proximity to, the superior articulation pit of atlas 124 of the atlas 110" and the "profile of the foramen magnum of the skull 100."

The partial profile t10 of the foramen magnum of the skull 100 is represented on an actual X-ray film as a white line around the dens 132 of the axis 130. Consequently, the dens 132 of the axis 130 can be comparatively easily found in the film. The partial profile 10 of the outer periphery of the foramen magnum 102 can be easily found by making an attempt to find a substantially circular line in the vicinity of the dens 132.

Figure 15:
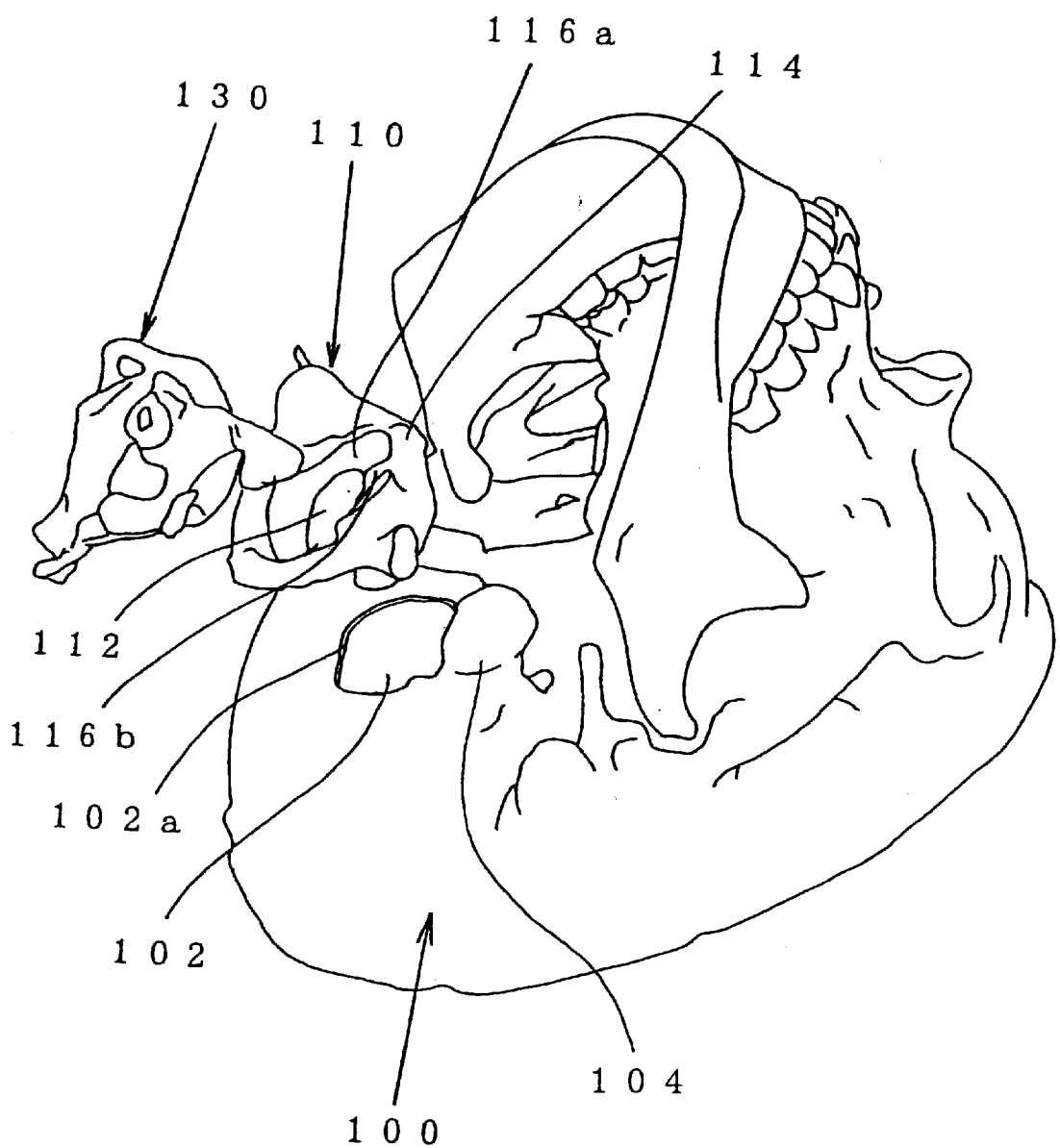
FIG. 15 is an exploded perspective view showing the skull, the atlas (the first cervical vertebra), and the axis (the second cervical vertebra)
Figure 16:
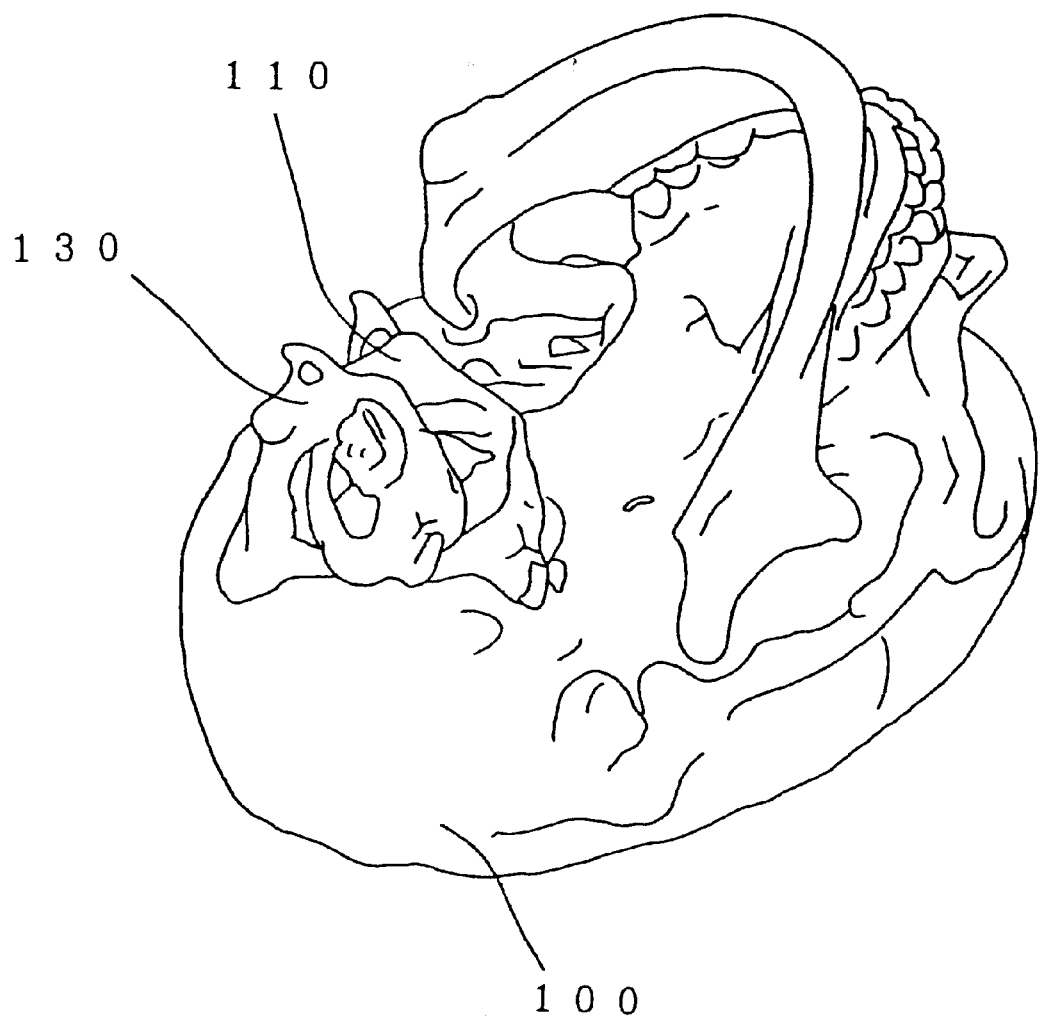
FIG. 16 is a view similar to FIG. 15, but showing the actual positional relationship between the atlas and the axis in the skull.

FIG. 15 is an exploded view showing the skull 100, the atlas 110, and the axis 130. They are actually in the positional relationship such as that shown in FIG. 16. FIG. 17 shows the skull 100 when viewed from the bottom, and FIG. 18 is a plan view of the atlas 110. The atlas 110 has an anterior arch 114 in the direction of the front side of the patient and a posterior arch 118 in the direction of the rear side of the patient. Further, an aperture 112 is formed in substantially the center of the atlas 110. The above-described step S11 corresponds to a process of defining points of origin on both sides (simply referred to as a point-of-origin-determination step throughout the specification).

Next, as shown in FIGS. 9 and 10, a line L1 which connects the points P1 and P2 is drawn, and a line L2 which connects the points P1 and P3 is drawn (step S12 as shown in FIG. 1).

A point of intersection of the line L1 and the anterior arch 114 of the atlas vertebra 110 is defined as a listing point P4, and a point of intersection of the line L2 and the anterior arch 114 of the atlas 110 is defined as a listing point P5 (step S13 as shown in FIG. 1). More specifically, as shown in FIG. 10, the listing point P4 is a point of intersection of the line L1 and a profile t14 of the upper end of the anterior arch 114, and P5 is a point of intersection of the line L2 and the profile t14 of the upper end of the anterior arch 114. This step S13 corresponds to a listing point determination step.

Here, a distance between the point P1 and the listing point P4 is determined so as to equal a distance between the point P1 and the listing point P5. If the distance between the point P1 and a tentative point P4a—which is a point of intersection of the profile t14 and the line L1—and the distance between the point P1 and a tentative point P5a—which is a point of intersection of the profile t14 and the line L2—are not equal to each other, either the tentative point P4a or the tentative point P5a, whichever point has a higher probability, is prioritized. For example, if the tentative point P4a is much clearer than the tentative point P5 on the profile t14 of the upper end of the anterior arch 114, the tentative point P4a is defined as the listing point P4. A listing point P5 is defined on the line L2 in such a way that the points P5 and P4 are equidistant from the point P1. Specifically, in FIG. 10, although the point of intersection of the line L2 and the profile t14 of the upper end of the anterior arch 114 is defined as a tentative point P5a, the listing point P5 is defined so as to be spaced the same distance away from the point P1 as is the listing point P4.

The listing points P4 and P5 are symmetrical about a point of contact between the occipital condyle and the superior articular surface of the atlas 110. As will be described later, the center of the foramen magnum is determined from these listing points.

As shown in FIG. 10, circular patterns which are equidistant from the respective listing points P4 and P5 are drawn on the film, and two points of intersections of the circular patterns are respectively defined as P20 and P21 (an equidistant point determination step). A listing line which connects the two points P20 and P21 is drawn as a line L3 (S14 shown in FIG. 1). The line L3 is a bisector of the acute angle which the line L1 forms with the L2 and extends substantially in the longitudinal direction of the base posterior view. A step of drawing the listing line L3 corresponds to a listing line determination step.

A line which connects the listing points P4 and P5 obtained in step S13 is drawn as a superior line L4 (S15).

The point of center of a foramen transversarium 120 on the left side is defined as a point P6, and the point of center of another foramen transversarium 120 on the right side is defined as a point P7. A line that connects the points P6 and P7 is drawn as an atlas line L5 (S16 shown in FIG. 1). The points P6 and P7 are referred to as foramen transversarium points, and the atlas line L5 is referred to as an inter-foramen-transversarium line. The step S16 corresponds to an inter-foramen-transversarium line determination step. As shown in FIG. 10, a point of intersection of the listing line L3 and the atlas line L5 is defined as a point P8. The foramen transversariums 120 are openings formed in both sides of the atlas 110. More specifically, as shown in FIG. 18, the foramen transversariums 120 are formed in the vicinity of the respective transverse processes 122 provided at both ends of the atlas 110.

An explanation will now be given of another method of determining a point of origin on each side of the base posterior view.

Figure 19:
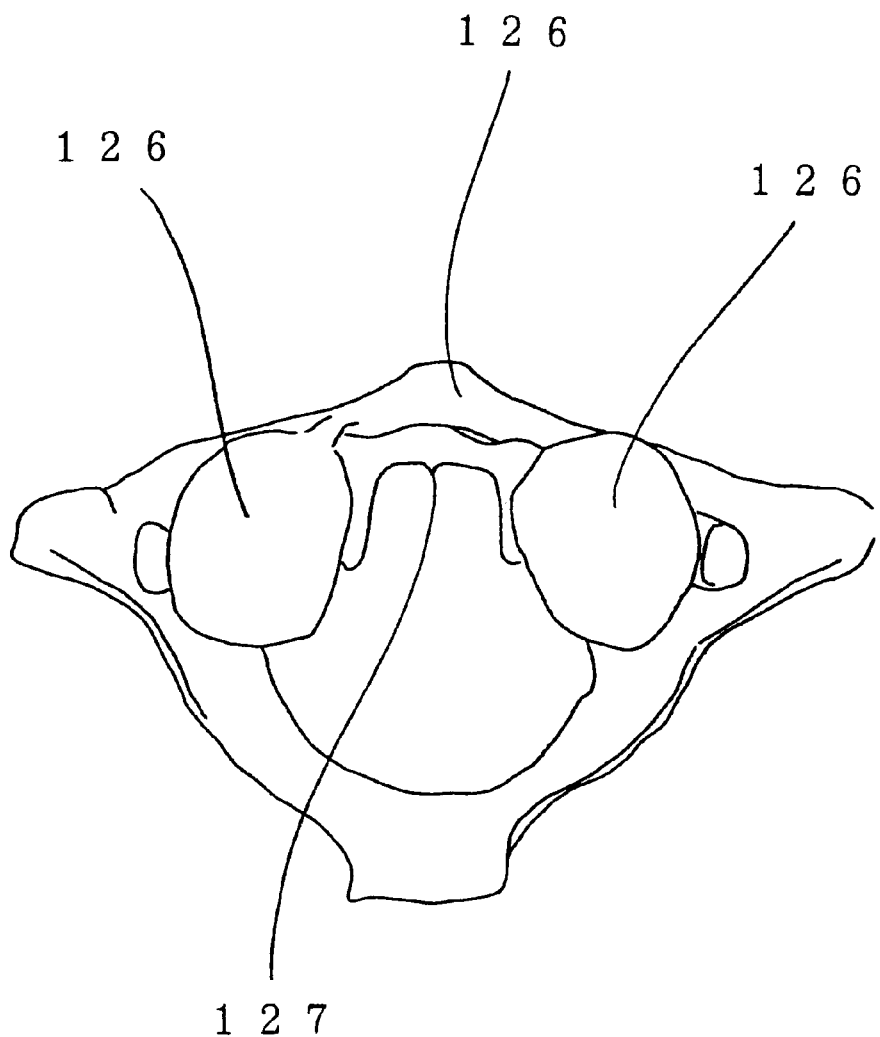
FIG. 19 is a bottom view showing the atlas.
Figure 22:
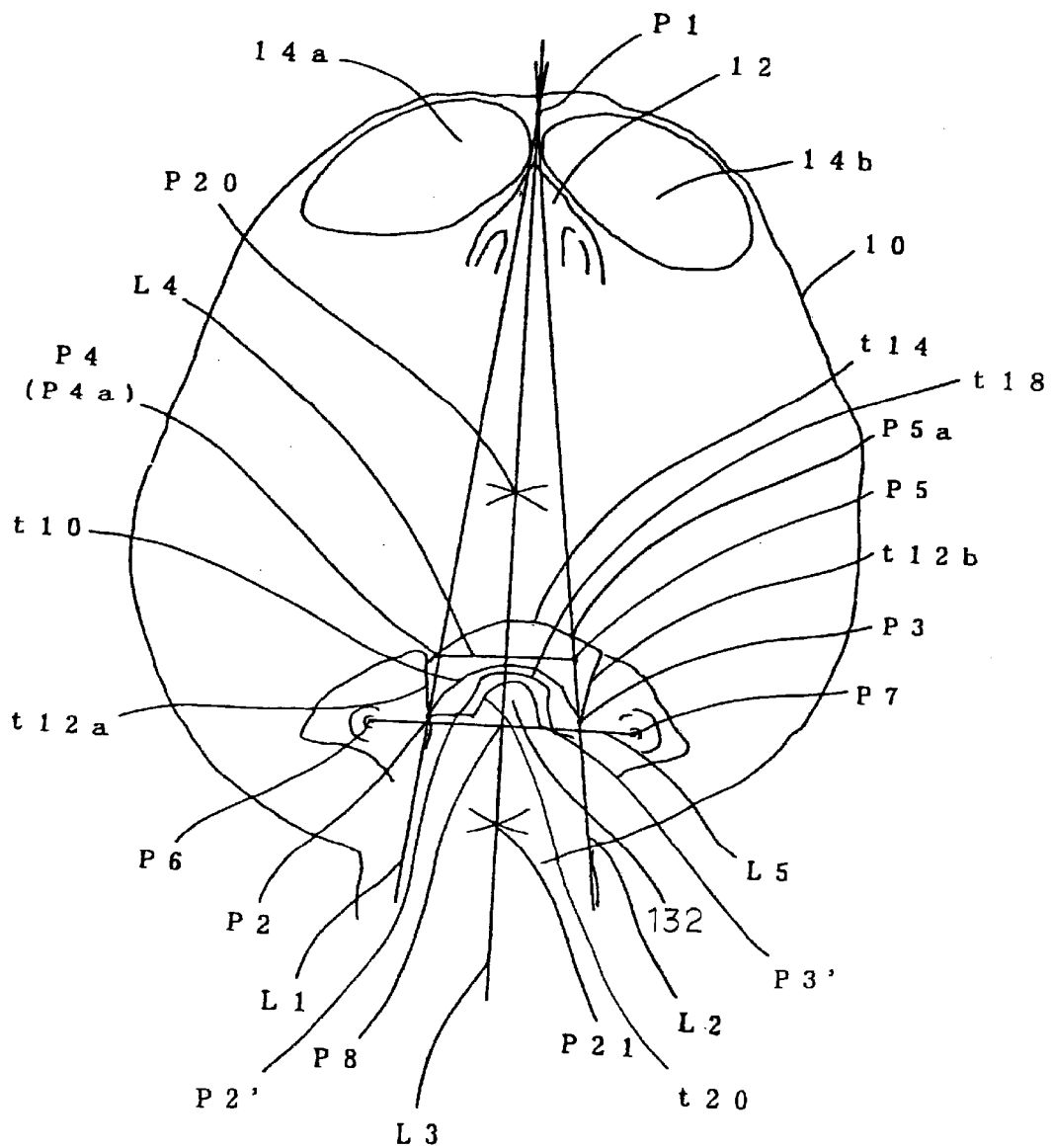
FIG. 22 is a diagrammatic representation for explaining a method of measuring the amount of dislocation of cervical vertebrae in accordance with still another embodiment of the present invention.
Figure 23:
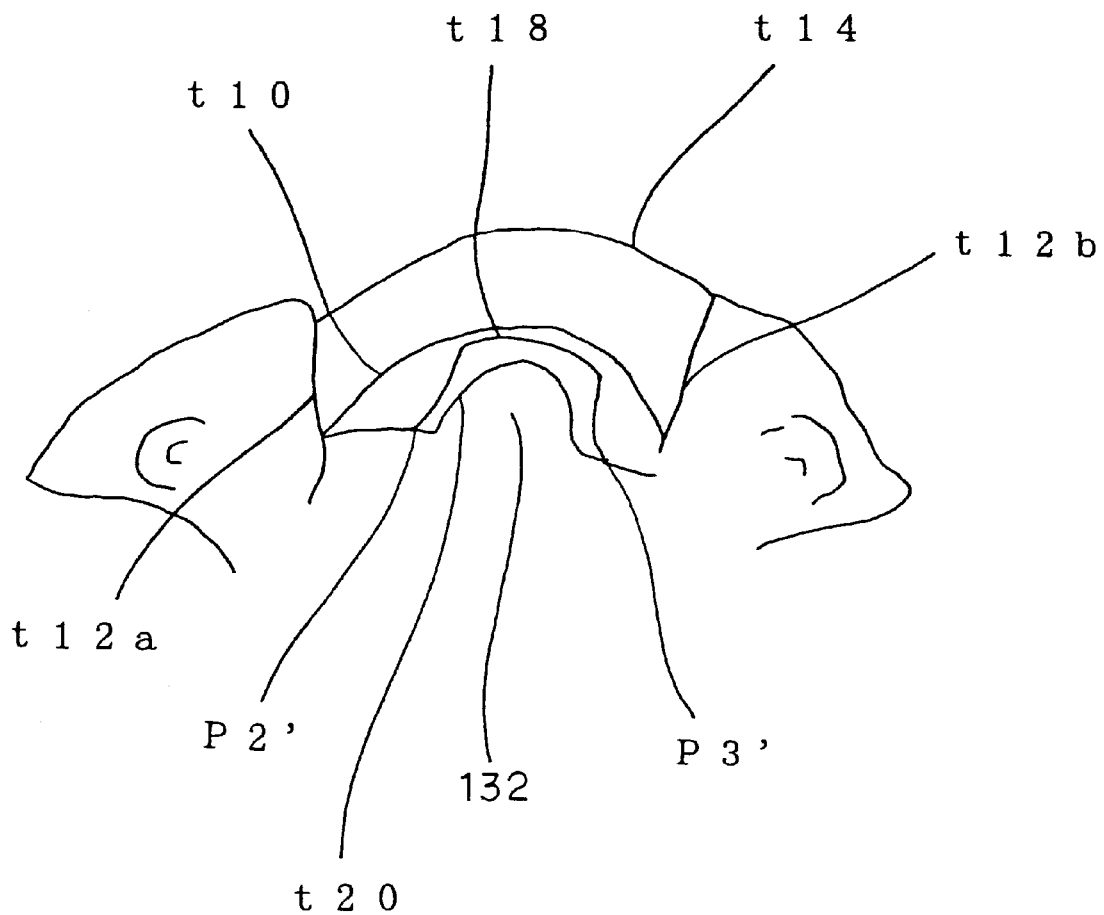
FIG. 23 is an enlarged view showing the principle elements shown in FIG. 22.
Figure 24:
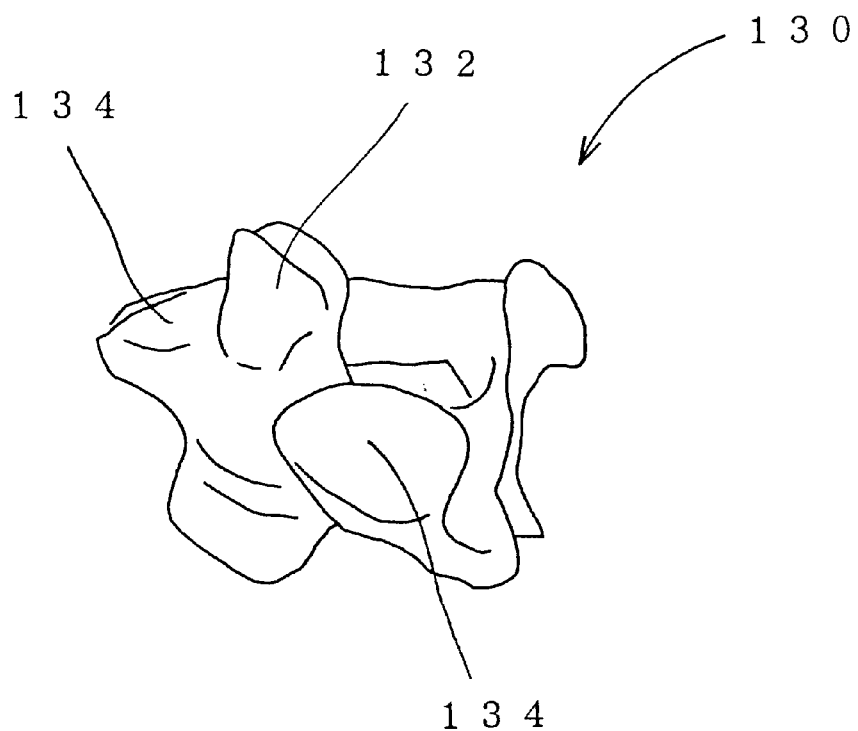
FIG. 24 is a perspective view showing the axis.
Figure 25:
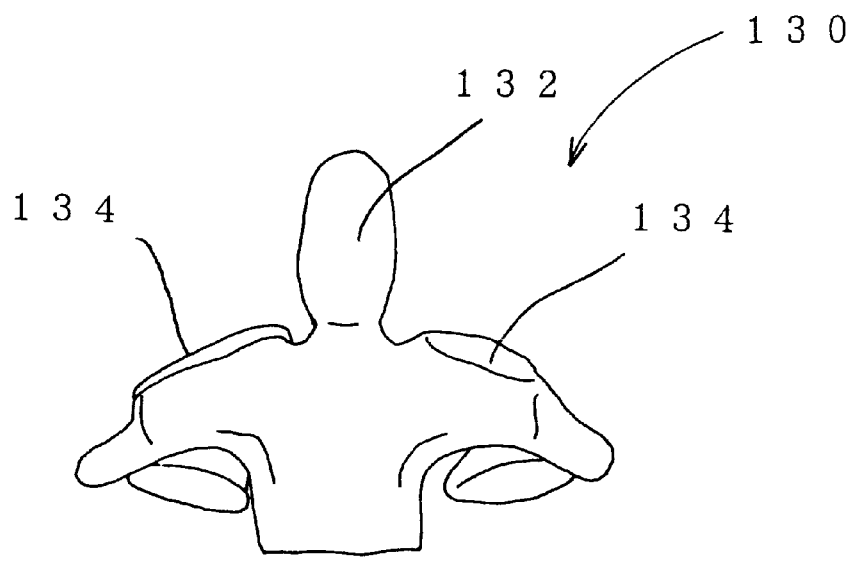
FIG. 25 is a front view showing the axis.

As shown in FIGS. 22 and 23, a profile t18 of the inside of the inferior articulation of the atlas is indicated around the dens 132. More specifically, the profile t18 is the profile of an inside area 127 of an inferior articulation 126 shown in FIG. 19. A profile t20 of the front portion of the superior articular surface 134 and the dens 132 of the axis 130 is indicated in the area where the dens 132 is to be displayed. Throughout the specification, a term "front" is used herein to define the orientation of elements of the human body, provided that the face is on the front side of the human body. Consequently, the dens 132 is on the front side of the atlas 130. As shown in FIGS. 23 and 24, the base posterior view looks as if the axis 130 were seen at an angle of elevation from a position below the axis 130, and the profile of the superior articular surface 134 and the dens 132 corresponds to the profile t20. These profiles t18 and t20 can be readily found in an X-ray film of the base posterior view.

Figure 2:
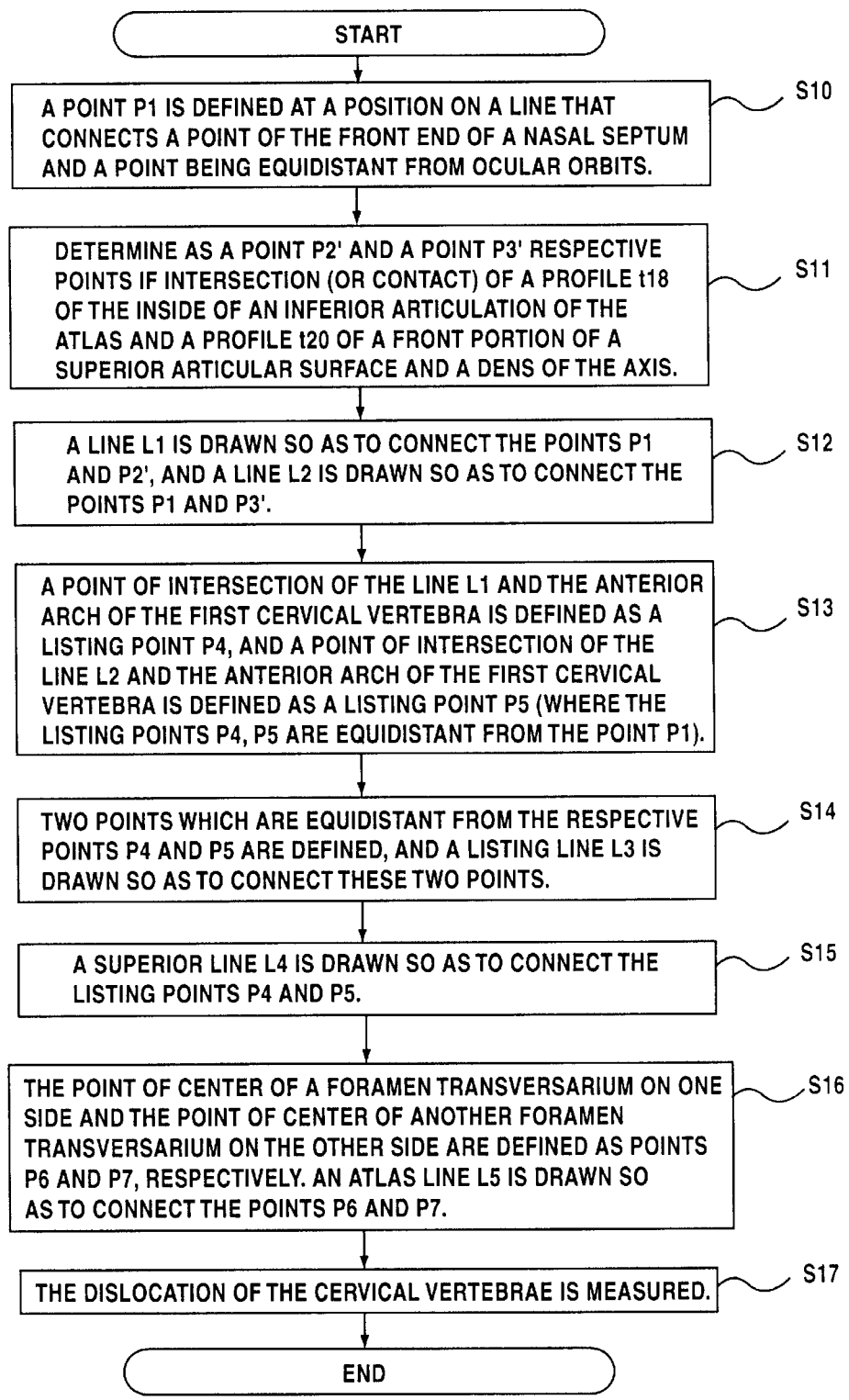
FIG. 2 is a flowchart illustrating a method of measuring the amount of dislocation of cervical vertebrae in accordance with another embodiment of the present invention.

As shown in FIG. 22, points of intersection of the profile t18 and the profile t20 are defined as a point P2' and a point P3' (S11 shown in FIG. 2). If there are not any points of intersection between the profile t18 and the profile t20, but if there are points of contact between the profiles t18 and t20, the points of contact are defined as the point P2' and point P3'.

As previously mentioned, after the points P2' and P3' which serve as the points of origin have been determined, processing analogous to that previously executed with regard to the points P2 and P3 are performed in the manner as shown in FIG. 2. The line L1 connecting the points P2' and P3' and the line L2 connecting the points P3' and the point P1 are determined (see S12 shown in FIG. 2). The listing points P4 and P5 are determined on the basis of the lines L1 and L2 (S13 shown in Fig. 2). A listing line L3 is drawn on the basis of the listing points P4 and P5 (S14 shown in FIG. 2). Further, a superior line L4 is drawn so as to connect together the listing points P4 and P5, and an atlas line L5 is further drawn (S16 shown in FIG. 2).

Explanations have been given of the method of determining the points of origin such as that represented by step S11 shown in FIG. 1 or such as that represented by S11 shown in FIG. 2. More specifically, in step S11 shown in FIG. 1, the points of intersection (or contact) of the profiles t12a, t12b of the right and left portions of an occipital atlanto articulation and the partial profile t10 of a foramen magnum of the skull are defined. In S11 shown in FIG. 2, the points of intersection of the profile t18 of the inside of the inferior articulation of the atlas and the profile t20 of the front portion of the superior articular surface and the dens of the axis are determined. As a matter of course, if these two methods are simultaneously employed, the points P2, P3 may differ from the points P2', P3'. In such a case, there is a possibility that any one pair of or both of the two pairs of points will be incorrect. Therefore, it is desirable to go back to step S11. If there is not a match between the points even after the processing has been reexecuted predetermined times, the subsequent steps are executed by selection of any one of the two pairs of points.

Upon completion of the foregoing processing operations, the dislocation of the cervical vertebrae is determined through use of the lines obtained in the previously-described steps (S17 shown in FIGS. 1 and 2). One example of the determination of the dislocation of the cervical vertebrae will be provided below.

Figure 3:
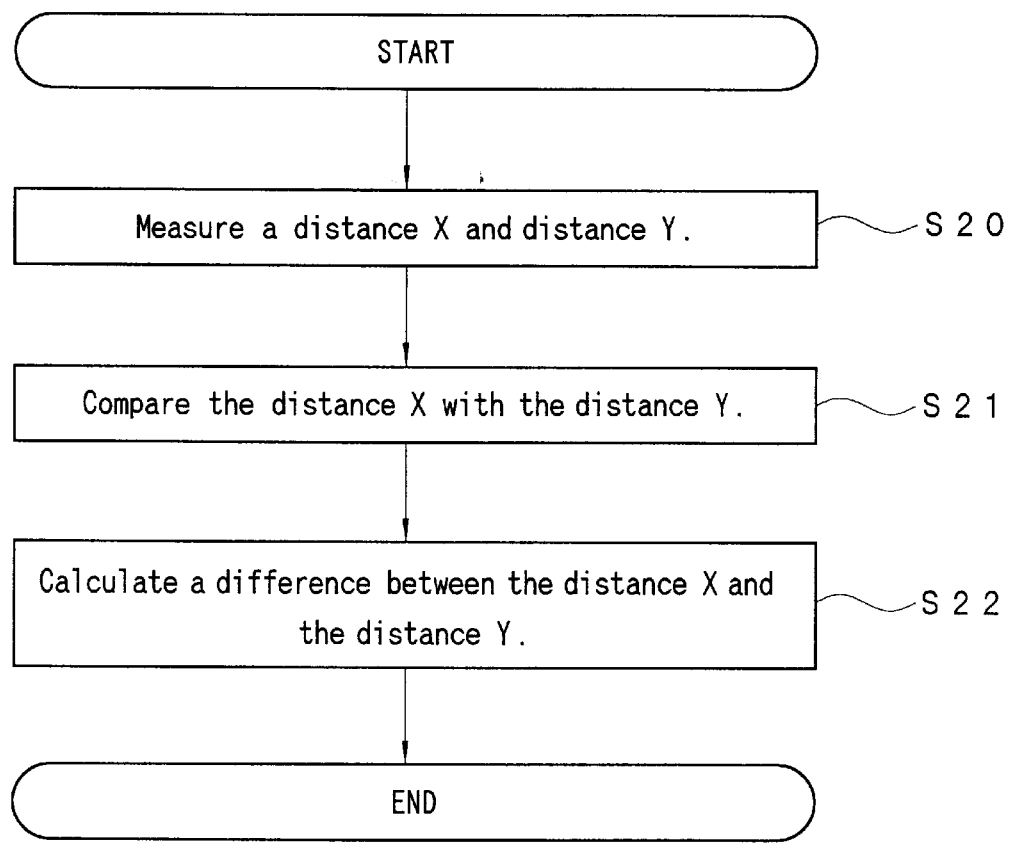
FIG. 3 is a flowchart illustrating one example of step S17 in FIG. 1.
Figure 12:
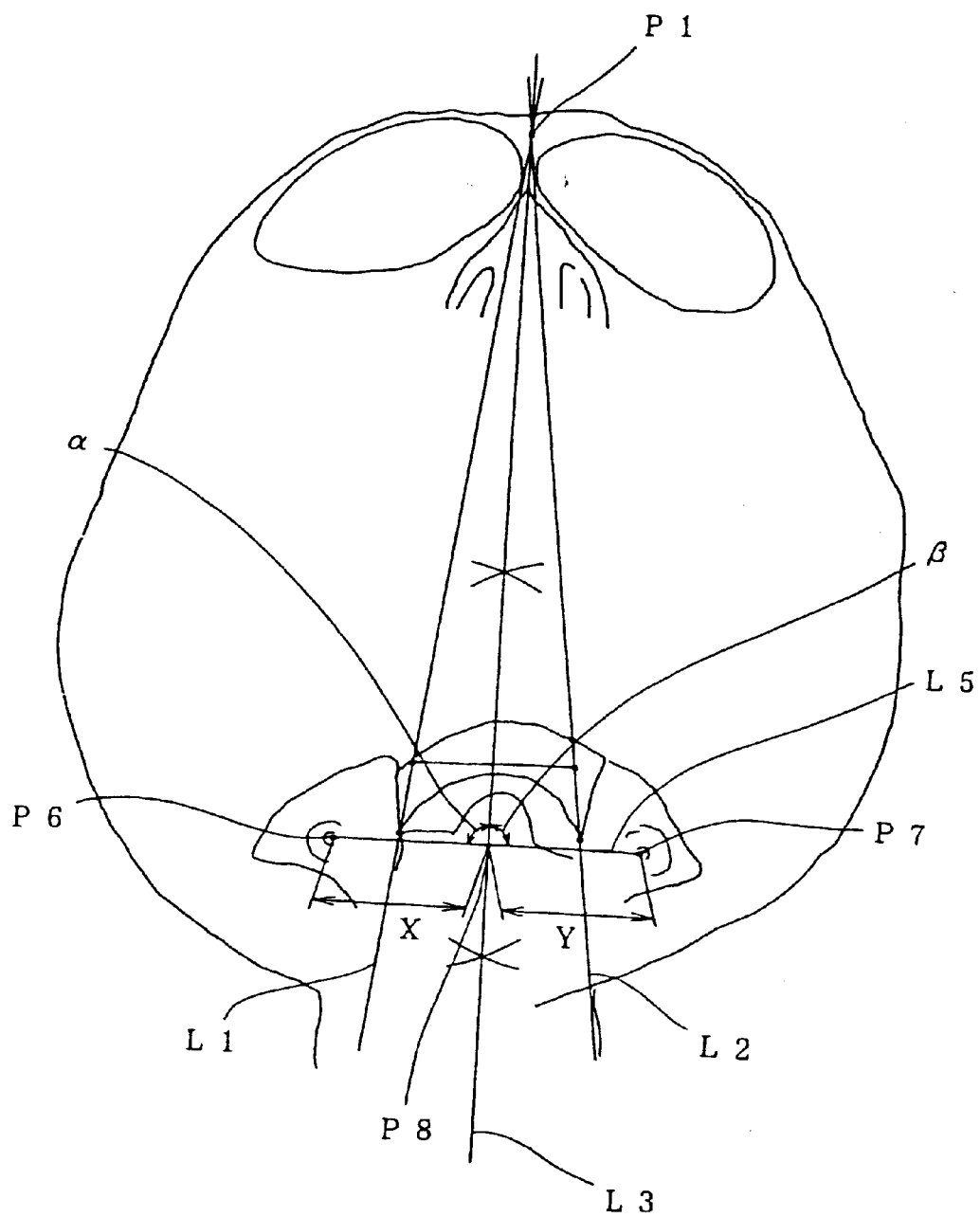
FIG. 12 is a view similar to FIG. 11.

First, by reference to FIG. 3, the measurement of the amount of lateral dislocation of the atlas 110 is described. The lateral dislocation of the atlas 110 is the dislocation of the atlas 110 in its transverse direction with reference to the skull 100. As shown in FIG. 12, a distance X between the points P6 and P8 and a distance Y between the points P7 and P8 are measured (S20 shown in FIG. 3). The lateral dislocation of the atlas 110 is measured in accordance with the results of such measurement. More specifically, the distance X and the distance Y are compared with each other (S21 shown in FIG. 3), whereby the direction in which the atlas 110 is dislocated is determined. For example, if the distance X is larger than the distance Y, the atlas 110 is dislocated to the leftward direction in FIG. 12. In short, the atlas 110 is dislocated to the left in the body of the patient. Conversely, if the distance Y is larger than the distance X, the atlas 110 is dislocated to the rightward direction in FIG. 12.

A difference "m" between the distance X and the distance Y is calculated (S22 shown in FIG. 3). This difference "m" designates the amount of lateral dislocation of the atlas 110. For example, if the distance X is larger than the distance Y by "m," the atlas 110 is dislocated to the left by "m" in FIG. 12. Conversely, if the distance Y is larger than the distance X by "m," the atlas 110 is dislocated to the right by "m" in FIG. 12. In this way, the lateral dislocation of the atlas 110 can be measured. The round of steps shown in FIG. 3 correspond to the step of calculation of the lateral dislocation of the atlas.

Although the explanation has been given of the measurement of the lateral dislocation of the atlas 110 by means of the distances X and Y, the method of the present invention is not limited to this example. For instance, the lateral dislocation of the atlas 110 may be determined by the comparison of a distance between the point P6 and a point determined by drawing a line perpendicular to the listing line L3 from the point P6 and a distance between the point P7 and a point determined by drawing a line perpendicular to the listing line L3 from the point P7. Although the difference between the distances X and Y is calculated in the foregoing embodiment, a ratio of the distance X to the distance Y may be obtained in place of the difference.

Next, in reference to FIG. 4, the determination of the rotational dislocation of the atlas 110 will be described. The rotational dislocation of the atlas 110 used herein represents the dislocation of the atlas 110 in its rotational direction with reference to the skull 100. As shown in FIG. 12, an angle α which the listing line L3 forms with the atlas line L5 in relation to the point P6 and an angle β which the listing line L3 forms with the atlas line L5 in relation to the point P7 are measured, whereby the rotational dislocation of the atlas 110 is determined.

Figure 4:
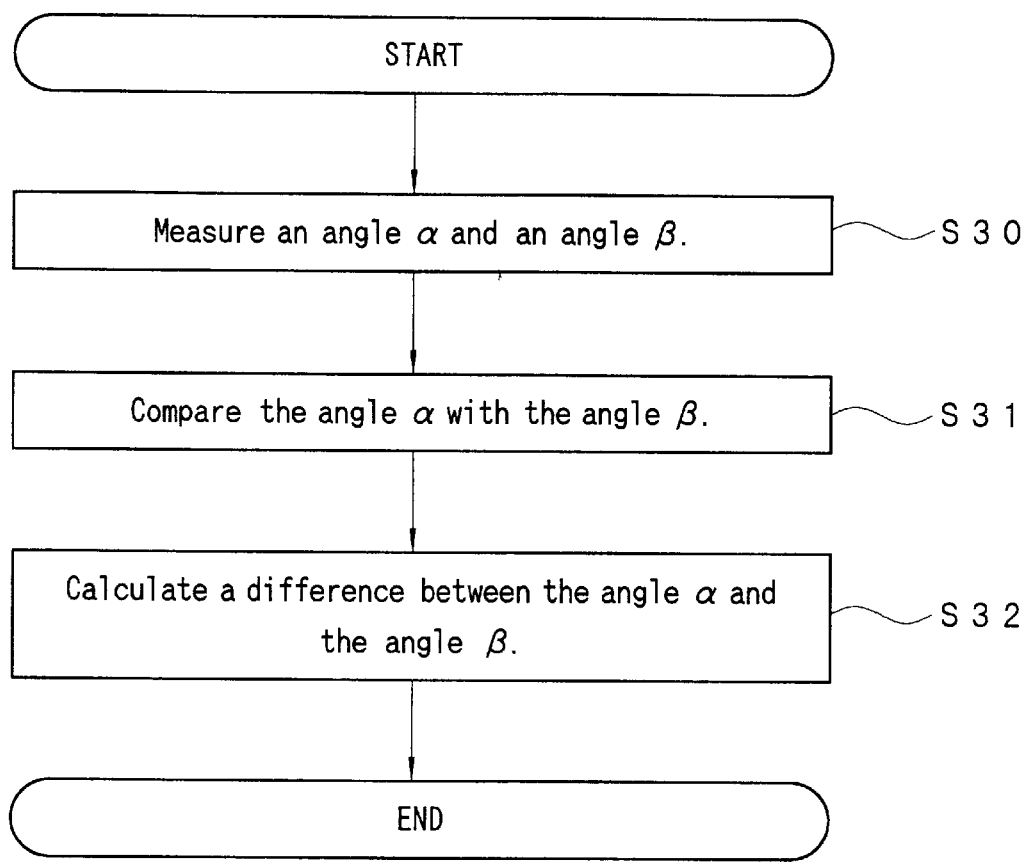
FIG. 4 is a flowchart illustrating one example of step S17 in FIG. 1.

More specifically, the angles α and, β are measured (S30 shown in FIG. 4), and the thus-measured angles α and β are initially compared with each other (S31 shown in FIG. 4). The result of such comparison between the angles α and β shows a direction in which the atlas 110 is twisted. If the angle β is larger than the angle α, the atlas 110 is twisted counterclockwise in FIG. 12. In the case where the atlas 110 is twisted counterclockwise, the atlas 110 is actually twisted counterclockwise in the body of the patient. Conversely, if the angle α is larger than the angle β, the atlas 110 is twisted clockwise in FIG. 12.

A difference "n" between the angles α and β is calculated (S32 shown in FIG. 4). The difference "n" represents the amount of rotational dislocation of the atlas 110. If the angle β is larger than the angle α by the amount "n," the atlas 110 is twisted counterclockwise by n/2 in FIG. 12. For instance, if the angle α is 89° and the angle β is 91°, the atlas 110 is twisted through 1°. In this way, the rotational dislocation of the atlas 110 can be measured. The series of steps shown in FIG. 4 correspond to a step of calculating the rotational dislocation of the atlas.

The amount of rotational dislocation of the atlas 110 may also be determined from the angle which the superior line L4 forms with the atlas line L5.

Figure 6:
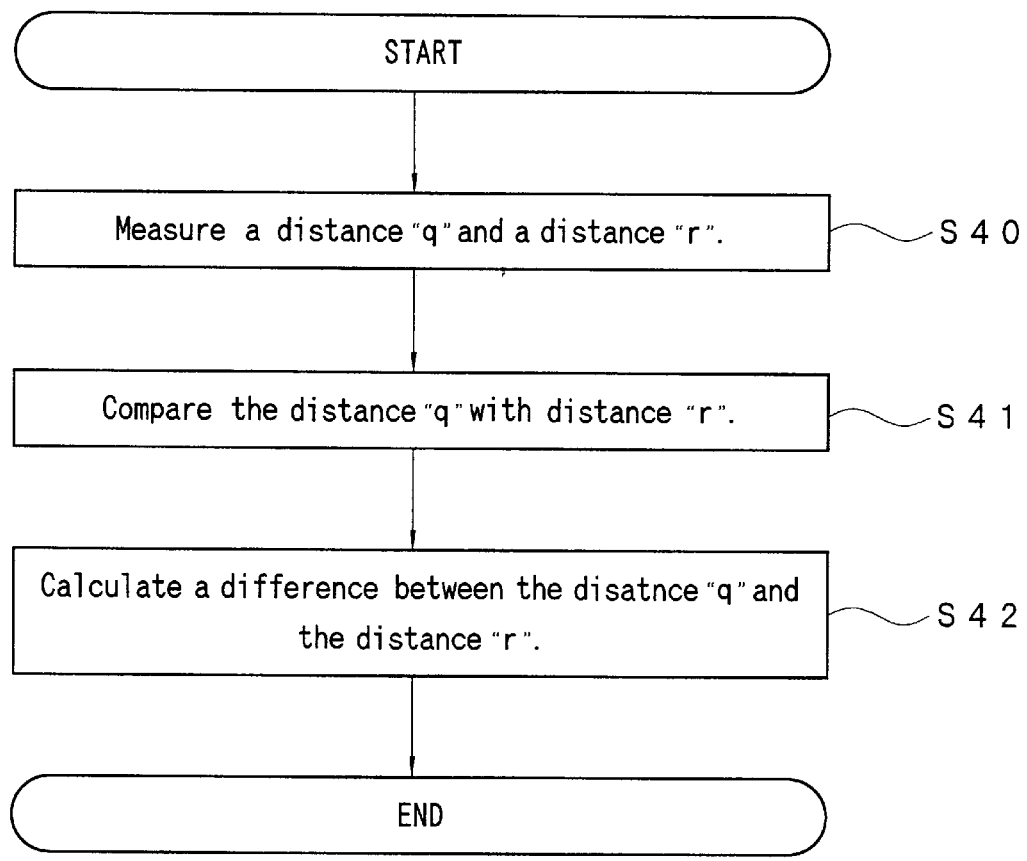
FIG. 6 is a flowchart illustrating one example of step S17 in FIG. 1.

In reference to FIG. 6, the measurement of the amount of lateral dislocation of the axis 130 is described. The lateral dislocation of the axis 130 is the dislocation of the axis 130 in its transverse direction with reference to the skull 100. In addition to the previously-described measurement information, additional measurement information, as will be described below, are provided for the base posterior view.

Figure 5:
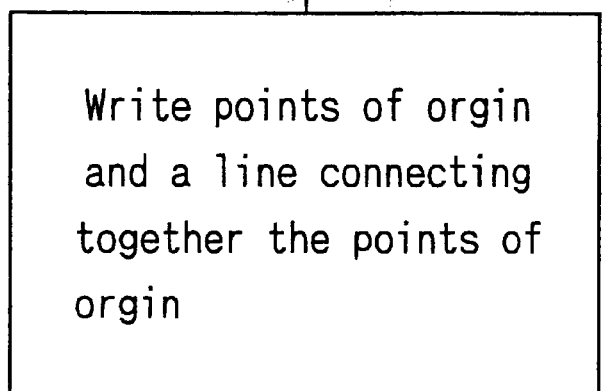
FIG. 5 is a flowchart illustrating a part of the method of measuring the amount of dislocation of the axis.

More specifically, as shown in FIG. 5, a step of writing, on the base posterior view, points of origin or a line connecting together the points of origin must be provided between the steps S16 and S17 in FIGS. 1 and 2.

Figure 13:
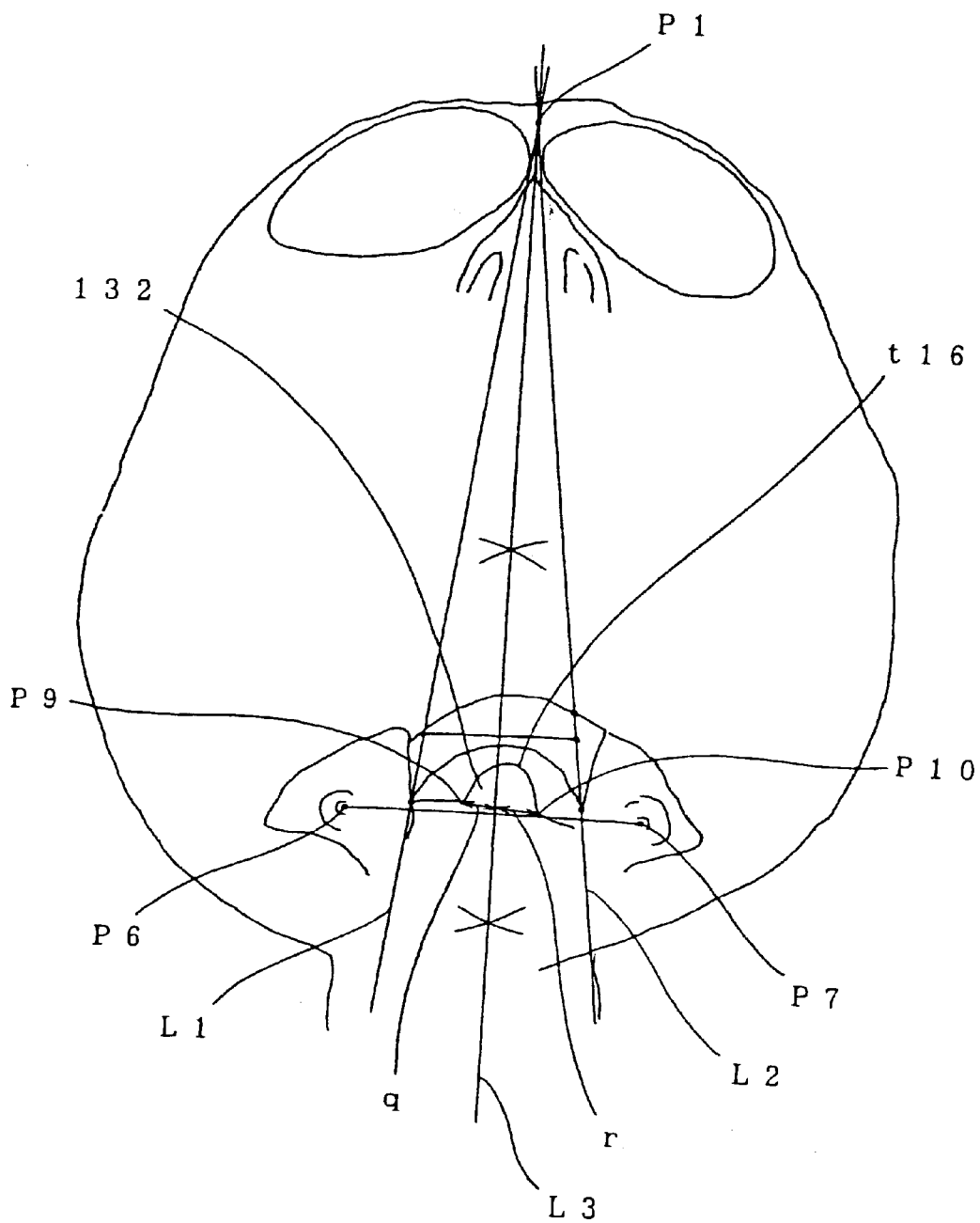
FIG. 13 is a view similar to FIG. 12.
Figure 14:
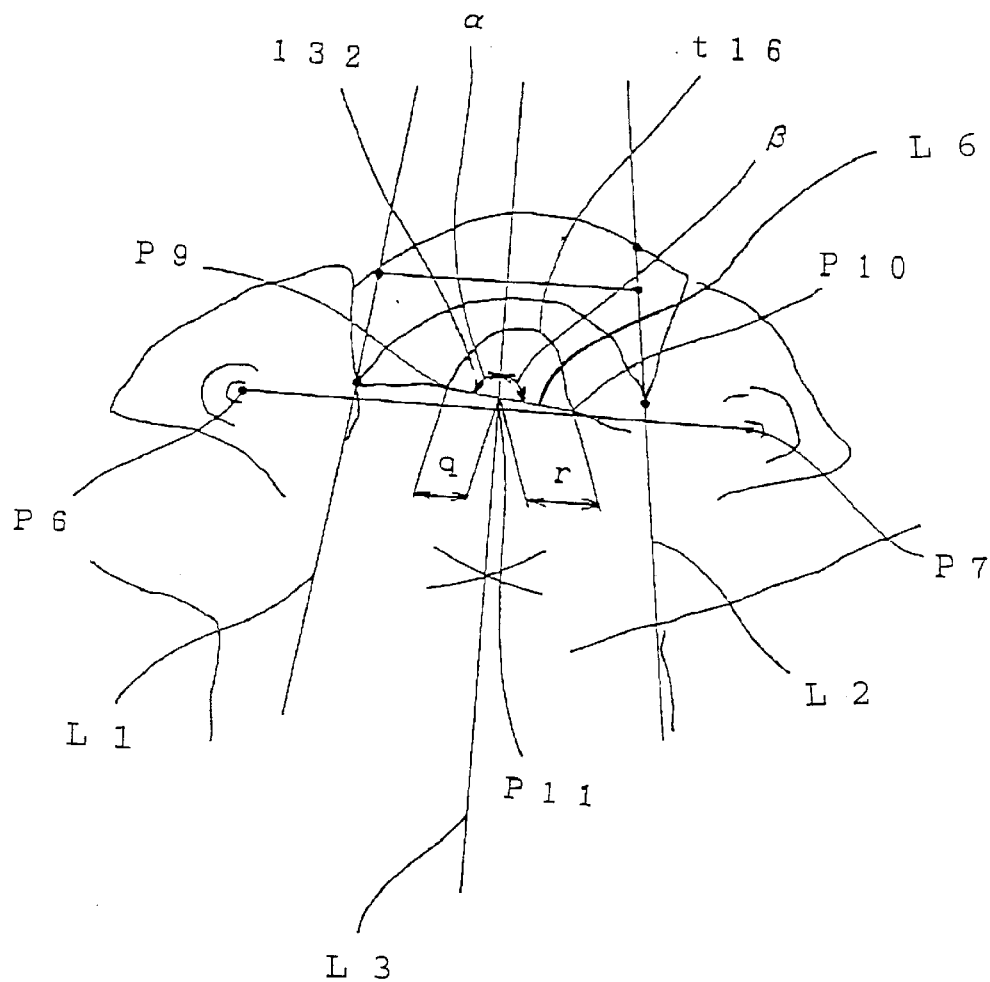
FIG. 14 is an enlarged view of the principle element shown in FIG. 13.

As shown in FIG. 13, a profile t16 of the dens 132 of the axis 130 is defined, and points of origin of the profile t16, i.e., points P9 and P10, are determined. The points P9 and P10 are connected by a line L6 (simply referred to as a point-of-origin connection line throughout the specification). As shown in FIG. 14, a point of intersection of the point-of-origin connection line L6 and the listing line L3 is determined as a point P11. A distance "q" between the points P11 and P9 and a distance "r" between the points P11 and P10 are measured (S40 shown in FIG. 6). The lateral dislocation of the axis 130 is measured in accordance with the result of such measurement.

More specifically, the distance "q" and the distance "r" are compared with each other (S41 shown in FIG. 6), whereby the direction in which the axis 130 is dislocated is determined. For example, if the distance "q" is larger than the distance "r," the axis 130 is dislocated to the left in FIG. 13. In short, the axis 130 is dislocated to the left in the body of the patient. Conversely, if the distance "r" is larger than the distance q, the axis 130 is dislocated to the right in FIG. 13.

A difference "u" between the distance "q" and the distance "r" is calculated (S42 shown in FIG. 6). This difference "u" designates the amount of lateral dislocation of the axis 130. For example, if the distance "r" is larger than the distance "q" by "u," the axis 130 is dislocated to the right by "u" in FIG. 13. As described above, the lateral displacement of the axis 130 can be measured. Although the difference between the distances X and Y is calculated in the foregoing example, a ratio of the distance X to the distance Y may be obtained in place of the difference.

The round of steps shown in FIG. 6 correspond to a step of calculating the lateral dislocation of the axis.

As shown in FIGS. 13 and 14, if it is desired to measure the amount of rotational dislocation of the axis 130 with reference to the skull 100, it may be determined from the angle of tilt which the listing line L3 forms with the point-of-origin connection line L6. More specifically, an angle α which the listing line L3 forms with the line connecting the points P9 and P11 is compared with an angle β which the listing line L3 forms with the line connecting the points P11 and P10. For the case shown in FIG. 14, the angles α and β are measured and compared with each other.

The amount of rotational dislocation of the axis 130 is calculated from a difference between the angles α and β. As is the case with the atlas 110, the angles α and β are measured in the manner as shown in FIG. 4. As described above, the rotational dislocation of the axis 130 can be measured. The step of measuring the rotational dislocation of the axis 130 corresponds to a step of calculating the rotational dislocation of the axis.

The dislocation of the axis 130 with reference to the atlas 110 is determined from the angle which the point-of-origin connection line L6 forms with the atlas line L5. The previously-described step of determining the line connecting between the points of step corresponds to a point-of-origin connection line determination step.

The amounts of dislocation of the atlas 110 and the axis 130 were measured, and the atlas 110 and the axis 130 of the patient were adjusted (treated) in accordance with the thus-measured amounts of dislocation, whereby considerable effects were acknowledged (the term "adjust" used herein represents the principal therapy practiced in the field of chiropractic.). This means that the amounts of dislocation have been accurately measured. Particularly, in treatment in the field of chiropractic, determination as to which of the dislocation of the atlas 110 or the axis 130 is large in amount is important. According to the measurement method of the present invention, it is possible to determine which of the dislocation of the atlas or the axis is large in amount by the comparison between the amounts of dislocation of the atlas and the axis, whereby information very beneficial to chiropractic treatment is obtained. Further, even if the V-shaped area defined between the profile of the fundus of the occipital bone and the profile of the occipital condyle is not seen in an X-ray film, the amount of dislocation of the cervical vertebrae can be accurately measured according to the measurement method of the present invention.

The foregoing description of the preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

I claim:

1. A method of measuring the amount of dislocation of the cervical vertebrae of a person, the method including:
    an end point determination step of defining, on the base posterior view, an end point on a line which connects a point representing the front end of the nasal septum to a point being equidistant from a pair of ocular orbits;
    a point-of-origin-determination step of determining, on each side of the base posterior view, a point of intersection or contact of the profile of a foramen magnum of a skull and the region where a condyle of the skull is joined to, or in close proximity to, a superior-articular-pit-of-atlas of the atlas; and
    a bisector determination step of defining, on the base posterior view, a bisector of the angle which a line connecting the front end point to one of the points of origin forms with respect to another line connecting the front end point to the other one of the points of origin.

2. The method of measuring the amount of dislocation of the cervical vertebrae of a person as defined in claim 1, wherein the bisector determination step comprises:
    a given point determination step of determining a point by selection of any one of a pair of points of intersection between the pair of lines connecting the front end point to the pair of points of origin and the profile of the anterior arch of the atlas, and determining another given point on the line, in which an unselected point of intersection is located, at a distance away from the front end point, the distance corresponding to the length between the selected point of intersection and the front end point;
    an equidistant point determination step of determining two points on the base posterior view, the two points being equidistant from each of the pair of given points; and
    a line determination step of determining a bisector on the base posterior image by drawing a line so as to connect together the two equidistant points.

3. The method of measuring the amount of dislocation of the cervical vertebrae of a person as defined in claim 2, further comprising an inter-foramen-transversarium line determination step of defining, on the image of the base posterior view, points of foramen transversariums which represent points of the substantial center of the foramen transversariums of the atlas, and of drawing a line connecting these points.

4. The method of measuring the amount of dislocation of the cervical vertebrae of a person as defined in claim 2, further comprising a point-of-origin connection line step of drawing a line connecting together a pair of points of origin which represent the base ends of the profile of the dens of the axis.

5. The method of measuring the amount of dislocation of the cervical vertebrae of a person as defined in claim 2, wherein the image of the base posterior view is displayed on an X-ray film, and the points and lines defined in claim 2 are written on the X-ray film.

6. The method of measuring the amount of dislocation of the cervical vertebrae of the man as defined in claim 1, further comprising an inter-foramen-transversarium line determination step of defining, on the image of the base posterior view, points of foramen transversariums which represent points of the substantial center of the foramen transversariums of the atlas, and of drawing a line connecting these points.

7. The method of measuring the amount of dislocation of the cervical vertebrae of a person as defined in claim 6, further comprising a step of calculating the lateral dislocation of the atlas, in which the amount of lateral dislocation of the atlas is calculated by measurement of a distance between one point of foramen transversarium and the point of intersection of the inter-transversarium line and the bisector and of a distance between the other point of foramen transversarium and the point of the intersection.

8. The method of measuring the amount of dislocation of the cervical vertebrae of a person as defined in claim 6, further comprising a step of calculating the rotational dislocation of the atlas, in which the amount of rotational dislocation of the atlas is calculated by measurement of an angle which the inter-foramen-transversarium line forms with respect to the line connecting the point of intersection to one point of foramen transversarium and another angle which the inter-foramen-transversarium line forms with respect to the line connecting the point of intersection to the other point of foramen transversarium.

9. The method of measuring the amount of dislocation of the cervical vertebrae of a person as defined in claim 6, further comprising a point-of-origin connection line step of drawing a line connecting together a pair of points of origin which represent the base ends of the profile of the dens of the axis.

10. The method of measuring the amount of dislocation of the cervical vertebrae of a person as defined in claim 6, wherein the image of the base posterior view is displayed on an X-ray film, and the points and lines defined in claim 3 are written on the X-ray film.

11. The method of measuring the amount of dislocation of the cervical vertebrae of a person as defined in claim 1, further comprising a point-of-origin connection line step of drawing a line connecting together a pair of points of origin which represent the base ends of the profile of the dens of the axis.

12. The method of measuring the amount of dislocation of the cervical vertebrae of a person as defined in claim 11, further comprising:

a step of calculating the lateral dislocation of the atlas, in which the amount of lateral dislocation of the axis is calculated by measurement of a distance from one of the points of origin to the point of intersection of the bisector and the point-of-origin connection line, as well as of a distance from the other one of the points of origin to the point of intersection of the bisector and the point-of-origin connection line.

13. The method of measuring the amount of dislocation of the cervical vertebrae of a person as defined in claim 11, further comprising a step of calculating the rotational dislocation of the axis, in which the amount of rotational dislocation of the axis is calculated by measurement of the angle which the bisector forms with respect to the point-of-origin connection line.

14. The method of measuring the amount of dislocation of the cervical vertebrae of a person as defined in claim 11, wherein the image of the base posterior view is displayed on an X-ray film, and the points and lines defined in claim 4 are written on the X-ray film.

15. The method of measuring the amount of dislocation of the cervical vertebrae of a person as defined in claim 1, wherein the image of the base posterior view is displayed on an X-ray film, and the points and lines defined in claim 1 are written on the X-ray film.

16. A method of measuring the amount of dislocation of the cervical vertebrae of a person, the method including:

an end point determination step of determining, on the image of the base posterior view, an end point on a line which connects a point representing the front end of the nasal septum to a point being equidistant from a pair of ocular orbits;

a point-of-origin-determination step of determining, on each side of the base posterior view, a point of intersection or contact of the profile of an inferior articular surface of the atlas and the profile of a front portion of the superior articular surface and a dens of the axis; and a bisector determination step of defining, on the image of the base posterior view, a bisector of the angle which a line connecting the front end point to one of the points of origin forms with respect to another line connecting the front end point to the other one of points of origin.

17. The method of measuring the amount of dislocation of the cervical vertebrae of a person as defined in claim 16, wherein the bisector determination step comprises:

a given point determination step of determining a point by selection of any one of a pair of points of intersection between the pair of lines connecting the front end point to the pair of points of origin and the profile of the anterior arch of the atlas, and determining another given point on the line, in which an unselected point of intersection is located, at a distance away from the front end point, the distance corresponding to the length between the selected point of intersection and the front end point;

an equidistant point determination step of determining two points on the base posterior view, the two points being equidistant from each of the pair of given points; and a line determination step of determining a bisector on the base posterior image by drawing a line so as to connect together the two equidistant points.

18. The method of measuring the amount of dislocation of the cervical vertebrae of a person as defined in claim 17, further comprising an inter-foramen-transversarium line determination step of defining, on the image of the base posterior view, points of foramen transversariums which represent points of the substantial center of the foramen transversariums of the atlas, and of drawing a line connecting these points.

19. The method of measuring the amount of dislocation of the cervical vertebrae of a person as defined in claim 17, further comprising a point-of-origin connection line step of drawing a line connecting together a pair of points of origin which represent the base ends of the profile of the dens of the axis.

20. The method of measuring the amount of dislocation of the cervical vertebrae of a person as defined in claim 17, wherein the image of the base posterior view is displayed on an X-ray film, and the points and lines defined in claim 6 are written on the X-ray film.

21. The method of measuring the amount of dislocation of the cervical vertebrae of a person as defined in claim 16, further comprising an inter-foramen-transversarium line determination step of defining, on the image of the base posterior view, points of foramen transversariums which represent points of the substantial center of the foramen transversariums of the atlas, and of drawing a line connecting these points.

22. The method of measuring the amount of dislocation of the cervical vertebrae of a person as defined in claim 21, further comprising a step of calculating the lateral dislocation of the atlas, in which the amount of lateral dislocation of the atlas is calculated by measurement of a distance between one point of foramen transversarium and the point of intersection of the inter-transversarium line and the bisector and of a distance between the other point of foramen transversarium and the point of the intersection.

23. The method of measuring the amount of dislocation of the cervical vertebrae of a person as defined in claim 21, further comprising a step of calculating the rotational dislocation of the atlas, in which the amount of rotational dislocation of the atlas is calculated by measurement of an angle which the inter-foramen-transversarium line forms with respect to the line connecting the point of intersection to one point of foramen transversarium and of another angle which the inter-foramen-transversarium line forms with respect to the line connecting the point of intersection to the other point of foramen transversarium.

24. The method of measuring the amount of dislocation of the cervical vertebrae of a person as defined in claim 21, further a point-of-origin connection line step of drawing a line connecting together a pair of points of origin which represent the base ends of the profile of the dens of the axis.

25. The method of measuring the amount of dislocation of the cervical vertebrae of a person as defined in claim 21, wherein the image of the base posterior view is displayed on an X-ray film, and the points and lines defined in claim 6 are written on the X-ray film.

26. The method of measuring the amount of dislocation of the cervical vertebrae of a person as defined in claim 16, further comprising a point-of-origin connection line step of drawing a line connecting together a pair of points of origin which represent the base ends of the profile of the dens of the axis.

27. The method of measuring the amount of dislocation of the cervical vertebrae of a person as defined in claim 26, further comprising:

a step of calculating the lateral dislocation of the atlas, in which the amount of lateral dislocation of the axis is calculated by measurement of a distance from one of the points of origin to the point of intersection of the bisector and the point-of-origin connection line, as well as of a distance from the other one of the points of origin to the point of intersection of the bisector and the point-of-origin connection line.

28. The method of measuring the amount of dislocation of the cervical vertebrae of a person as defined in claim 26, further comprising a step of calculating the rotational dislocation of the axis, in which the amount of rotational dislocation of the axis is calculated by measurement of the angle which the bisector forms with respect to the point-of-origin connection line.

29. The method of measuring the amount of dislocation of the cervical vertebrae of a person as defined in claim 26, wherein the image of the base posterior view is displayed on an X-ray film, and the points and lines defined in claim 6 are written on the X-ray film.

30. The method of measuring the amount of dislocation of the cervical vertebrae of a person as defined in claim 16, wherein the image of the base posterior view is displayed on an X-ray film, and the points and lines defined in claim 6 are written on the X-ray film.

* * * * *